Figure 1:
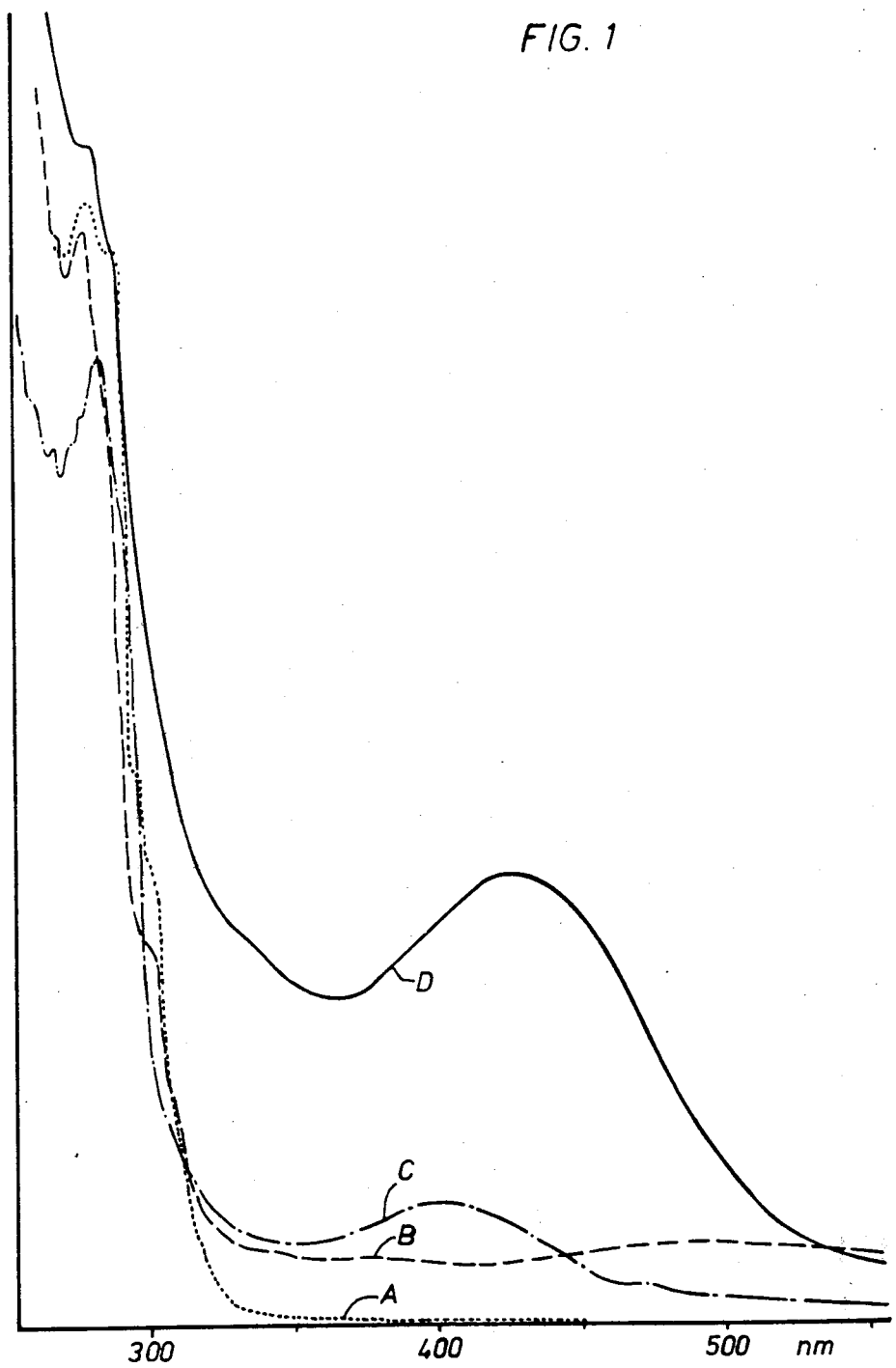

United States Patent [19]

Schnabel et al.

[11] 4,118,481
[45] Oct. 3, 1978

[54] DEAMINO DERIVATIVES OF THE KALLIKREIN-TRYPSIN INHIBITOR

[75] Inventors: Eugen Schnabel; Horst Dieter Schlumberger; Gerd Reinhardt; Ernst Truscheit, all of Wuppertal; Harald Tschesche, Groebenzell, all of Germany

[73] Assignee: Bayer Aktiengesellschaft, Leverkusen, Germany

[21] Appl. No.: 792,296

[22] Filed: Apr. 29, 1977

[30] Foreign Application Priority Data

Apr. 30, 1976 [DE] Fed. Rep. of Germany ....... 2619246

[51] Int. Cl.² ............... A61K 37/00; C07C 103/52; C07G 7/00
[52] U.S. Cl. ............................ 424/177; 260/112.5 R
[58] Field of Search ................ 260/112.5 R; 424/177

[56] References Cited

PUBLICATIONS

Anderer, F. A., et al., Ann. New York Acad. Sci. 146, 381 (1968).

Primary Examiner—Delbert R. Phillips
Assistant Examiner—Blondel Hazel
Attorney, Agent, or Firm—Burgess, Dinklage & Sprung

[57] ABSTRACT

A demaino kallikrein-trypsin inhibitor obtained from cattle organs is characterized by (a) 0 to 3 lysine residues and/or 3 to 6 arginine residues and/or 1 to 4 tyrosine residues; (b) the 10- and/or 21-tyrosine residues being unsubstituted or substituted by at least one nitro, nitroso or amino in the ortho position relative to the phenolic hydroxy group; and (c) having protease inhibitory activity of BPTI and elastase inhibition activity.

14 Claims, 6 Drawing Figures

DEAMINO DERIVATIVES OF THE KALLIKREIN-TRYPSIN INHIBITOR

The present invention relates to new deamino derivatives of the kallikrein-trypsin inhibitor obtained from cattle organs. Kallikrein-trypsin inhibitor obtained from cattle organs is hereinafter referred to as BPTI (Basic Pancreatic Trypsin Inhibitor [Kunitz]).

It has already been disclosed that BPTI [H. Kraut, E. K. Frey, E. Werle, Z. Physiol. Chem. 189, 97 (1930)], which is also termed the Kunitz inhibitor [M. Kunitz, H. H. Northrop, J. Gen. Physiol. 19, 991 (1936)], inhibits a number of physiologically significant enzymes, such as, for example, kininogenins (kininogenases), plasmin, chymotrypsin and trypsin (E. Werle in W. Brendel and G. L. Haberland: Neue Aspekte der Trasylol-Therapie 5, 9, F. K. Schattauer-Verlag Stuttgart-New York 1972; and H. Fritz, H. Tschesche, L. J. Greene, E. Truscheit (Editors): Proteinase Inhibitors (Bayer Symposium V), Proc. 2nd International Research Conference, Springer-Verlag Berlin-Heidelberg-New York 1974). BPTI is used as Aprotinin for the therapy and prophylaxis of states of shock and for the prophylaxis of post-operative and post-traumatic complications. Kassell and Chow, *Biochemistry* (Wash.) 5, 3449-3453 (1966) report the identification of the sequence of amino acids for BPTI as follows:

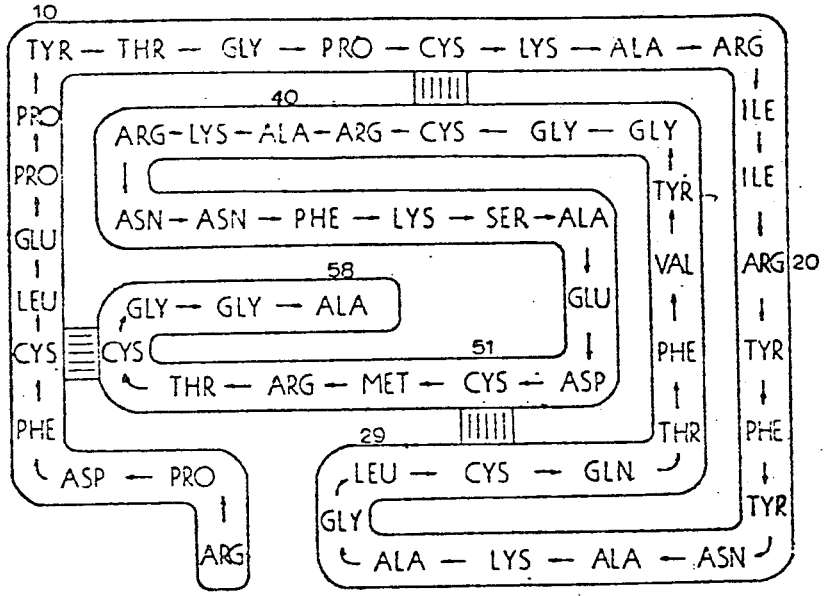

Others have confirmed this structure.

It is known that proteins can be deaminated by nitrous acid [L. A. Cohen, Ann. Rev. Biochemistry 37, 695 (1968)]. In addition, tyrosine can, by electrophilic substitution, be nitrated with the nitronium cation or nitrosated with the nitrosyl cation in the 3-position [O. Wagner, E. Irion, A. Arens and K. Bauer, Biochem. Biophys, Res. Comm. 37, 383 (1969)]. It is also known that BPTI can be deaminated at pH 5.0 with nitrous acid [F. A. Anderer and S. Hornle, Ann. New York acad. Sci. 146, 381 (1968)]. According to this publication, the amount of tryosine decreases as a function of the reaction time and lysine is fully decomposed, while arginine is not attacked. Furthermore, the decrease in the lysine content is accompanied by a complete loss of the inhibitory activity. Experimental details are not described in this publication.

According to the present invention, novel deamino derivatives of BPTI are provided, characterized by (a) 0 to 3 lysine residues and/or 3 to 6 arginine residues and/or 1 to 4 tyrosine residues;
(b) the 10- and/or 21-tyrosine residues being unsubstituted or substituted by at least one nitro, nitroso or amino in the ortho position relative to the phenolic hydroxy group; and
(c) having protease inhibitory activity of BPTI and elastase inhibitory activity.

The compounds of the invention are obtained when the kallikrein-trypsin inhibitor from cattle organs (BPTI), a nitro derivative of BPTI [B. Meloun, I. Frič and F. Šorm, Europ. J. Biochem. 4, 112 (1968)] or a deamido derivative of BPTI (obtained by reacting BPTI with a mineral acid under nitrogen for several days) is either:

(a) reacted in acid solution at a pH of from about 2 up to about 7 with a compound which supplies nitrous acid or nitrosyl ions, optionally in the presence of nucleophilic reagents and optionally under an inert gas, in an aqueous solution which can also contain organic solvents, at temperatures of from about −20° C. to about +30° C. Nitro derivatives or nitroso derivatives which may be obtained are reduced if appropriate and the products obtained from the reaction in acid solution are optionally fractionated according to methods which are in themselves known, or (b) reacted in aqueous and/or organic aqueous solution at a pH of from 1 to 12 with a diazonium compound at temperatures of from about −20° C. to about +30° C. Nitro groups which may arise in the nitro derivatives are reduced if desired and the products obtained from the reaction are optionally fractionated according to methods which are in themselves known.

It has been found that the new deamino derivatives of BPTI not only inhibit the enzymes chymotrypsin, cathepsin G, plasmin, trypsin and kininogenins (kininogenases), as does BPTI, but in addition they also inhibit elastases, for example from the pancreas or granulocytes. They can therefore be used, according to the invention, as medicaments for the therapy of diseases which are caused by overproduction of proteases as a result of increased liberation from the zymogens or of release during cell decomposition or by a deficiency or lack of natural endogenous inhibitors of these enzymes in organs and tissue fluids. Diseases which have this type of etiology are the various forms of shock and post-traumatic or post-operative complications, disorders in blood clotting and acute and chronic inflammatory reactions and, in particular, also chronic inflammatory reactions with necrotic and degenerative damage to connective tissue, such as pancreatitis and also vasculitides, glomerulonephritides, rheumatoid arthritis and other collagenoses caused by immune complexes and also arthritides caused by deposits due to metabolic processes (gout) but also degenerative changes in the elastic elements of vascular walls (arteriosclerosis) or in the lung (pulmonary emphysema).

It is indeed surprising that the deamino derivatives of BPTI, according to the invention, possess the known inhibitory activities of native BPTI and additionally possess a valuable inhibitory activity against elastases, since according to the state of the art (F. A. Anderer and S. Hornle, supra) the inhibitory action would have been expected to disappear on deamination with nitrous acid.

It has furthermore been found, surprisingly, that the deamination reaction, according to the invention, of BPTI and its derivatives, even under the pH value conditions indicated by Anderer and Hornle, supra, gives deamino derivatives which, in contrast to those described by Anderer and Hornle, are still inhibitory. In contrast to BPTI, all of the deamino derivatives according to the invention inhibit elastases from the pancreas and granulocytes. In respect of other proteases, such as chymotrypsin, pancreas kallikrein, plasma kallikrein, cathepsin G, plasmin and trypsin, the inhibition spectra for the individual derivatives differ qualitatively and/or quantitatively from those for BPTI. The inhibition of elastase is not the blocking of the substrate described by Pütter and Schmidt-Kastner [Biochim.Biophys.Acta 127, 538 (1966)], which takes place only with very high concentrations of BPTI, but is an inhibition of the enzyme.

This inhibitory action against elastase is the more surprising since it follows from the current state of the art [D. M. Blow, C. S. Wright, D. Kukla, A. Rühlmann, W. Steigemann and R. Huber J.Mol.Biol. 69, 137 (1972); R. Huber, D. Kukla, W. Steigemann, J. Deisenhofer and A. Jones in H. Fritz, H. Tschesche, L. J. Greene and E. Truscheit (Editors), Proteinase Inhibitors (Bayer-Symposium V) Proc. 2nd Intern. Res. Conference, page 484, Springer-Verlag Berlin-Heidelberg-New York 1974] that BPTI is bound, by its active centre (lysine-15 residue), like a substrate in the specifity pocket of those enzymes which are inhibited and thus blocks the enzyme activity. Even when the side chain of the lysine-15 residue is deaminated in all of the derivatives according to the invention, it is not to be expected, according to the current state of knowledge, that it would fit into the relatively small specificity pocket of the elastases [D. Shotten in H. Fritz and H. Tschesche (Editors), Proceedings of the International Research Conference on Proteinase Inhibitors, page 47, Walter de Gruyter (Berlin-New York 1971)].

Moreover, when the reaction is carried out according to process variant (b) at pH about 1 to 12, surprisingly, it is not, as was to be expected according to the data from the literature [L. A. Cohen, Ann. Rev. Biochemistry 37, 695 (1968)], the azo derivatives of BPTI which are obtained, but colorless compounds which, according to the results of amino-acid analysis have a reduced content of lysine and arginine but not of tyrosine (compare Table 2 below). This is the more astonishing since the diazonium compounds used according to the invention couple with acyl-tyrosine derivatives under analogous reaction conditions to give intensely colored azo derivatives. Thus, because of its specificity for histidine and tyrosine, diazonium tetrazole is recommended in the literature [H. Horinishi, Y. Hachimori, K. Kurihara and K. Shibata, Biochem. Biophys. Acta 86, 477 (1964)] in particular for the quantitative determination of these residues in proteins.

It can be seen from the absorption spectra (see FIG. 1) that coupling has not taken place either with tyrosine residues to give azo derivatives or with the free terminal amino group or with the $\epsilon$-amino groups of the lysine residues to give triazenes, which are also coloured [H. G. HIggins and K. J. Harrington, Arch. Biochem. Biophys. 85, 409 (1959)]. When BPTI or its derivatives are reacted with the diazonium compounds used according to the invention, the products formed are, in the main, deamino derivatives of BPTI which have relatively slightly reduced lysine and arginine contents (see Table 2, Examples 18 and 20).

In models for an acute inflammatory reaction, the deamino-BPTI derivatives according to the invention are superior to BPTI since, when the derivatives are used, not only is the same action as with BPTI achieved with distinctly smaller dosages but the inflammatory reaction is significantly inhibited even when the derivatives are administered several hours after setting of the inflammation noxa. A therapeutic action of this type cannot be achieved with BPTI on a single administration in a kaolin and aerosil model.

This changed action and effectiveness, compared with BPTI, of the deamino-BPTI derivatives according to the invention is attributable to the changed inhibition spectrum and other changed properties, such as a greater retention time and time of action in the body of the experimental animals. The BPTI derivatives according to the invention are therefore biologically clearly differentiated from BPTI.

Compared with BPTI, the deamino-BPTI derivatives according to the invention have superior biological properties. Their inhibitory actions on the elastases from the pancreas and granulocytes are of particular advantage and open up new possibilities for therapeutic use. An important role is played by pancreas elastase in pancreatitis [M. C. Geokas, H. Rinderknecht, V. Swanson, B. P. Vitron and B. J. Haverback, Clin.Res 16, 285 (1968)], by serum elastase in arteriosclerosis [U. Butturini and M. Langen, Klin.Wochenschr. 40, 472 (1962)] and by granulocyte elastase in acute and chronic inflammations with damage to the connective tissue [A. Janoff, Amer. J. Pathol. 68, 579 (1972)], in damage to the vascular walls [A. Janoff and J. D. Zeligs, Science 161, 702 (1968)] and also in necrotising diseases and degeneration of lung tissue, for example in the case of emphysemas [G. M. Turino, R. M. Senior, B. D. Garg, S. Keller, M. M. Levi and I. Mandl, Science 165, 709 (1969); H. E. Evans, M. M. Levi and I. Mandl, Amer. Rev. Respir. Dis. 101, 359 (1970) and A. Janoff, R. A. Sandhaus, V. D. Hospelhorn and R. Rosenberg, Proc.-Soc.Exptl.Biol.Med. 140, 516 (1972)]. The role of lyosomal enzymes and in particular of granulocyte elastase in inflammatory reactions which have an immunological cause [M. Koono, M. Muto and H. Hayashi, Tohoku J.Exptl. Med. 94, 231 (1968)], for example in rheumatoid arthritis [G. Weissmann and J. Spilberg, Athritis Rheumat. 11, 162 (1968)] is equally important.

The provision of the new deamino derivatives, according to the invention, of the kallikrein-trypsin inhibitor from cattle organs (BPTI) thus represents a substantial advance in the art.

The reaction of the kallikrein-trypsin inhibitor from cattle organs (BPTI), of nitro derivatives of BPTI or of deamido derivatives of BPTI in acid solution according to process variant (a) can be carried out both in a homogenous system and in a heterogeneous system. The reaction can be carried out even under conditions under which the conformation of the inhibitor is influenced, for example in the presence of dimethylsulphoxide. It is advantageous to employ the BPTI in concentrations of about 0.1 to about 10%, preferably of about 0.2 to about 5%. However, even higher inhibitor concentrations are possible. In order to carry out the reaction, the nitrosyl ion can be liberated from the donor with organic acids, preferably acetic acid. However, formic acid, citric acid, trifluoroacetic acid and p-toluenesulphonic acid are, for example, also suitable. Furthermore, inorganic acids, for example hydrochloric acid, hydrobromic acid, sulphuric acid and phosphoric acid, are also suitable. Liberation of the nitrosyl ion can be effected in a buffered or unbuffered medium. Suitable donors of nitrous acid or of the nitrosyl ion are salts of nitrous acid, especially the alkali metal nitrites; mixed anhydrides, such as nitrosyl chloride or nitrosylsulphuric acid, or organic derivatives of nitrous acid, such as, for example, the alkyl esters, e.g. $C_1$-$C_6$ alkyl esters, especially ethyl nitrite, tert.-butyl nitrite or isoamyl nitrite, are also suitable. In order to carry out the reaction, either the agent which supplies the nitrosyl can be added to the mixture of the inhibitor and the acid or acid solution, or the acid or acid solution can be added to the mixture of the inhibitor and the nitrosyl ion donor. In certain circumstances it is advantageous to carry out the reaction in the presence of additives, such as guanidine hydrochloride, urea or other acid amides and/or detergents.

During the reaction, nitrosation of the tyrosine residues in the 10- and/or 21-positions can also take place, in addition to the deamination of the lysine and arginine residues. If oxygen is not excluded during the reaction and/or the working up of the reaction mixture, nitration of the tyrosine residues also additionally takes place and the extent of this is dependent on the reaction conditions and the conditions of working up and can be determined by measuring the extinction of the reaction products at 425 nm. Nitro derivatives of the deaminated inhibitor are also obtained when nitro derivatives of BPTI, which can also be deamidised, are used as the starting materials for the deamination reaction.

Nitration can be prevented when the deamination reaction and the working up of the reaction mixture are carried out under an inert gas or while applying a vacuum. The inert gas can be dispensed with during working up if the pH value of the reaction mixture is adjusted, after the reaction, to about 7.5 to about 12 and preferably to about 8.0 to about 10.5.

Suitable additives for suppressing the electrophilic nitration and/or nitrosation of the tyrosine residues during the deamination reaction are compounds — such as, for example, phenol — which are more highly nucleophilic than the phenolic group of the tyrosine residues, O. Wagner, E. Irion, A. Arens and K. Bauer, Biochem. Biophys. Res. Comm. 37, 383 (1969).

Deamino derivatives of BPTI which have amino groups on the 10 and/or 21 tyrosine residues are obtained when the corresponding nitro derivatives are reduced. This reduction can advantageously be carried out with, for example, sodium dithionite according to known methods [compare M. Sokolovsky, J. F. Riordan, B. L. Vallee, Biochem. Biophys, Res. Comm. 27, 20 (1967)].

Mixtures of different components result from the reactions. The composition of the mixtures is dependent on the reaction conditions and can be regulated via the concentration of the reactants, the acidity of the medium, the temperature control and the reaction time and by adding denaturants and protective substances. The mixtures can be separated by ion exchange chromatography. Thus, for example, when the deamination of BPTI is carried out with sodium nitrite in a solution acidified with acetic acid, after a reaction time of 1 to 24 hours, under the conditions indicated in Example 1, mixtures are formed which can be separated into several components by ion exchange chromatography on gels which consist of crosslinked dextran and contain sulphopropyl groups. The lysine and arginine contents of individual components are given in Table 1 below.

Table 1

Lysine and arginine contents of BPTI and deamino BPTI derivatives which were obtained after different reaction times

| Substance | Reaction time (hours) | Lysine residues/ inhibitor (mol/mol) | Arginine residues/ inhibitor (mol/mol) |
|---|---|---|---|
| BPTI (native) | — | 4 | 6 |
| Component I | | 0 | 4 |
| Component II | | 1 | 5 |
| Component III | 1 | 2 | 5 |
| Component IV | | 3 | 5 |
| Component I' | | 0 | 3 |
| Component II' | | 0 | 4 |
| Component III' | 24 | 0 | 5 |
| Component IV' | | 1 | 5 |

As can be seen from Table 1, the arginine content of the deamination products is also reduced, in contrast to the data given by Anderer and Hornle described above.

The following should be mentioned with regard to process variant (b) (reaction with diazonium salts):

Novel deamino compounds of BPTI are also obtained, according to the invention, when the inhibitor or its derivatives are reacted, at pH values of between about 1 and about 12, preferably at pH about 5.0 to about 11.5, with those diazonium compounds which, under the customary conditions [compare K. H. Schündehutte in Methoden der organischen Chemie (Methods of Organic Chemistry) (Houben-Weyl), Volume 10, 3, 213, Georg Thieme Verlag, Stuttgart 1965, E. Müller, O. Bayer, H. Meerwein and K. Ziegler (Editors)] enter into virtually no coupling reactions with BPTI. Diazonium salts which are suitable for the reaction are obtained by diazotising preferably heterocyclic amines, for example 3-amino-1,2,4-triazole or 5-aminotetrazole. The diazonium salts are employed in about 1 to about 20 times the molar amount, relative to BPTI or its derivatives, preferably in an amount of about 2 to about 10 mols per mol of inhibitor. The reactions are carried out at temperatures of from about −20° C. to about +30° C., preferably from about 0° C. to about 10° C.

For these reactions, the concentrations of BPTI or its derivatives can be up to about 50%, preferably from about 5 to about 20%. The pH value of the reaction mixture can be between about 1 and about 12, preferably between about 5 and about 11, and is adjusted by adding bases, such as, for example, alkali metal hydroxides, carbonates or bicarbonates or alkaline earth metal hydroxides, carbonates or bicarbonates, tertiary amines (diethylaniline), N-methylmorpholine or triethanolamine, to the reaction mixture.

It can be seen from the absorption spectra (FIG. 1) that coupling has not taken place either with tyrosine residues to give azo derivatives or with the free terminal amino group or with the ε-amino groups of the lysine residues to give triazenes, which are also colored [H. G. Higgins and K. J. Harrington, Arch. Biochem. Biophys. 85, 409 (1959)]. When BPTI or its derivatives are reacted with the diazonium compounds used according to the invention mainly deamino derivatives of BPTI are formed which have relatively slightly reduced lysine and arginine contents (see Table 2, Examples 18 and 20).

organs (BPTI) are new. They can be characterized and differentiated from known substances by chemical, physicochemical, biochemical and biological properties. Use has been made of the following criteria:

(1) Amino-acid composition

The amino-acid composition was determined according to S. Moore, D. H. Spackmann and W. H. Stein [Anal. Chem. 30, 1185 (1958)]. The values for those amino-acid residues in some characteristic deamino-BPTI derivatives are given in Table 2 above.

Table 2

The contents of characteristic amino-acids determined from amino-acid analysis of some deamino-BPTI derivatives.

| Designation of the substance | Preparation, described in Example | mols of amino-acid residues/mols of BPTI derivatives[1] | | | | |
|---|---|---|---|---|---|---|
| | | glycine[2] | alanine[2] | tyrosine | lysine | arginine |
| BPTI[3] | | 6.09 | 6.00 | 3.80 | 4.08 | 6.01 |
| Deamino-BPTI derivative, frction A | | 6.18 | 6.66 | 2.11 | 0.27 | 3.51 |
| Deamino-BPTI derivative, fraction B | | 6.08 | 6.35 | 2.83 | 0 | 4.27 |
| Deamino-BPTI derivative, fraction C | 1 | 6.19 | 6.80 | 2.61 | 0 | 3.95 |
| Deamino-BPTI derivative, fraction D | | 6.81 | 5.81 | 2.53 | 0.18 | 4.44 |
| Deamino-BPTI derivative, fraction E | | 6.58 | 6.24 | 3.32 | 0 | 4.40 |
| Deamino-BPTI derivative, fraction F | | 6.31 | 5.92 | 2.98 | 0.25 | 4.50 |
| Deamino-BPTI derivative, fraction A | | 6.32 | 6.08 | 3.51 | 0.30 | 3.61 |
| Deamino-BPTI derivative, fraction B | | 5.98 | 5.61 | 3.76[4] | 0.26 | 3.84 |
| Deamino-BPTI derivative, fraction C | | 6.01 | 5.62 | 4.55[4] | 0.21 | 4.81 |
| Deamino-BPTI derivative, fraction D | 2 | 6.49 | 5.93 | 3.74 | 0.14 | 4.64 |
| Deamino-BPTI derivative, fraction E | | 6.82 | 5.58 | 4.72[4] | 1.06 | 4.88 |
| Deamino-BPTI derivative, fraction F | | 6.53 | 5.58 | 3.71 | 0.92 | 3.92 |
| Deamino-BPTI derivative, | 4 | 5.95 | 6.65 | 4.08[4] | 1.68 | 4.59 |
| Deamino-BPTI derivative, | 5 | 5.68 | 5.95 | 4.36[4] | 0.51 | 5.69 |
| Deamino-BPTI derivative, | 6 | 6.00 | 6.45 | 1.26 | 0.13 | 4.39 |
| Deamino-BPTI derivative, | 7 | 5.31 | 5.89 | 2.77 | 3.45 | 4.33 |
| Deamino-BPTI derivative, | 13 | 5.80 | 6.25 | 2.65 | 2.47 | 5.42 |
| Deamino-BPTI derivative, | 14 | 6.17 | 5.87 | 1.28 | 0.53 | 4.71 |
| Deamino-BPTI derivative, | 18 | 6.01 | 6.12 | 3.90 | 2.62 | 5.02 |
| Deamino-BPTI derivative, | 20 | 5.83 | 6.05 | 4.16 | 2.02 | 5.16 |

(1) The molecular weight of the derivatives was assumed to be 6,511 as for native BPTI.

(2) The alanine content and glycine content serve as an internal standard. Depending on the elution conditions during the amino-acid analysis, unknown substances, which can be stained with ninhydrin, are eluted together with glycine and/or alanine and these then simulate higher glycine contents and/or alanine contents.

(3) An amino-acid analysis of BPTI was also recorded for comparison. The theoretical values for the particular amino-acids are: Gly and Ala = 6.0; Tyr = 4.0; Lys = 4.0 and Arg = 6.0.

(4) A deamination product of lysine is eluted directly prior to tyrosine. The tyrosine peak in the chromatogram is therefore found either to be unsymmetrical or to be accompanied by a peak which is not quite resolved.

In FIG. 1 the spectra of some deamino derivatives of BPTI in 0.1 M tris-buffer of pH 8.0 are compared.

Curve A corresponds to a $1.44 \times 10^{-4}$ molar solution of BPTI,

Curve B corresponds to a $1.20 \times 10^{-4}$ molar solution of the reaction product of BPTI with diazotised aminotetrazole according to Example 18, Curve C corresponds to a $0.8 \times 10^{-4}$ molar solution of the reaction product of BPTI and nitrous acid according to Example 2 and Curve D corresponds to a $1.05 \times 10^{-4}$ molar solution of the reaction product of BPTI and nitrous acid according to Example 1.

The ordinate is a measure of the extinction and the abscissa indicates the wavelength in nm.

The deamino derivatives, according to the invention, of the kallikrein-trypsin inhibitor obtained from cattle (2) Electrophoretic properties Polyacrylamide gel electrophoresis Polyacrylamide gel electrophoresis of the deamino-BPTI derivatives was carried out in 10% polyacrylamide gel, which contained 0.8% of agarose, in the (LKB) Ultraphor electrophoresis apparatus at pH 8.6. Electrophoresis was carried out with water cooling and while keeping the voltage constant at 300 volts. In general, the running time was 2 hours. The methods indicated in the literature (A. J. Crowle "Immunodiffusion", 2nd edition, Academic Press New York-London, 1973, page 143–147) were slightly modified for the preparation of the polyacrylamide-agarose gel. After electrophoresis, the gels were stained (30–60 minutes) with a 0.1% solution of Amido-Black in 7.5% acetic acid. Excess Amido-Black not bonded to a protein was removed with 7.5% acetic acid.

Figure 6:
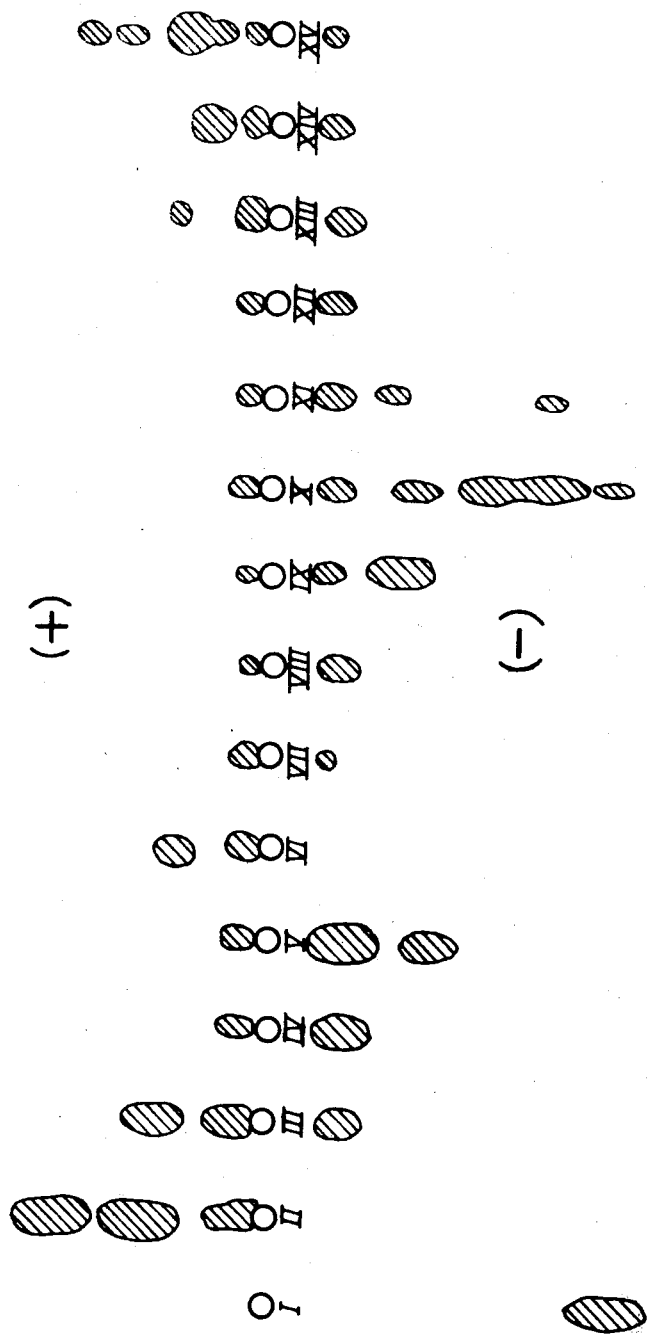

The electrophoretic mobilities of different BPTI derivatives are compared with that of BPTI in FIG. 6. The figure shows the pherograms of the following derivatives:

I BPTI;

II–V deamino-BPTI derivatives according to Example 1, fractions A, B, E and F;

VI–IX deamino-BPTI derivatives according to Example 2, fractions A, B, D and F;

X deamino-BPTI derivatives according to Example 4;

XI deamino-BPTI derivatives according to Example 5;

XII deamino-BPTI derivatives according to Example 10;

XIII deamino-BPTI derivatives according to Example 16;
XIV deamino-BPTI derivatives according to Example 13 and
XV deamino-BPTI derivatives according to Example 14.

(3) UV absorption spectrum

In order to detect the presence of nitrated and/or nitrosated tyrosine residues, the quotient of the extinctions at 280 nm and 425 nm was determined (Perkin-Elmer 124 spectrophotometer; the substances were dissolved in 0.1 M tris(hydroxymethyl)-aminomethane-HCl buffer, pH 8.0).

According to B. Meloun, I. Frič and F. Šorm [Europ. J. Biochem. 4, 112 (1968)], this quotient is ~2.5 for mononitro-BPTI and ~1.5 for dinitro-BPTI. Values higher than 3 indicate mixtures of BPTI derivatives which contain fractions which have not been nitrated.

(4) Protease inhibition spectrum

(a) Elastase inhibition

(α) Pancreas elastase inhibition

Crystalline pancreas elastase (pig) from Nutritional Biochemicals Corp. was used for the inhibition tests with the deamino-BPTI derivatives according to the invention. Elastin-Congo Red [M. A. Naughton and F. Sanger, Biochem. J. 78, 156 (1961)], soluble elastin [S. Keller and I. Mandl, Biochem. Med. 5, 342 (1971)] and, particularly advantageously, succinyl-L-alanyl-L-alanyl-L-alanine-p-nitroanilide [J. Bieth, B. Spiess and C. G. Wermuth, Biochem. Med. 11, 350 (1974)] were used as substrates. The synthetic peptide substrate makes it possible to carry out a simple colorimetric determination of the enzyme activity employed in the test. In the elastin-Congo Red test, the amount of elastase employed was about 1.1 nkat (compare Enzyme Nomenclature, Recommendations [1972] of the International Union of Pure and Applied Chemistry and the International Union of Biochemistry, 1973, Elsevier Amsterdam-New York, page 26–27); about 0.25 nkat of elastase was employed per assay when soluble elastin was used as the substrate and likewise when succinyl-L-alanyl-L-alanyl-L-alanine-p-nitroanilide was used. In order to carry out quantitative determinations of the elastase inhibitions, the amounts of enzyme indicated above were added to the substrate solution to which inhibitor solutions of defined concentration had been added. In order to ensure maximum formation of the complex, the enzyme and the inhibitor in some cases were pre-incubated for 15 to 30 minutes before the substrate was added. In the case of the elastin-Congo Red test, the hydrolysis of the substrate was determined by measuring the extinction, at 492 nm, of the soluble split products formed after a defined time. In the case of the test with soluble elastin, the rate of hydrolysis was ascertained by photometric determination of the soluble split products after a defined time stainable with ninhydrin. When succinyl-L-alanyl-L-alanyl-L-alanine-p-nitroanilide was used as the substrate, the hydrolysis was determined by continuous measurement of the extinction, at 410 nm, of the p-nitroaniline liberated.

Figure 2:
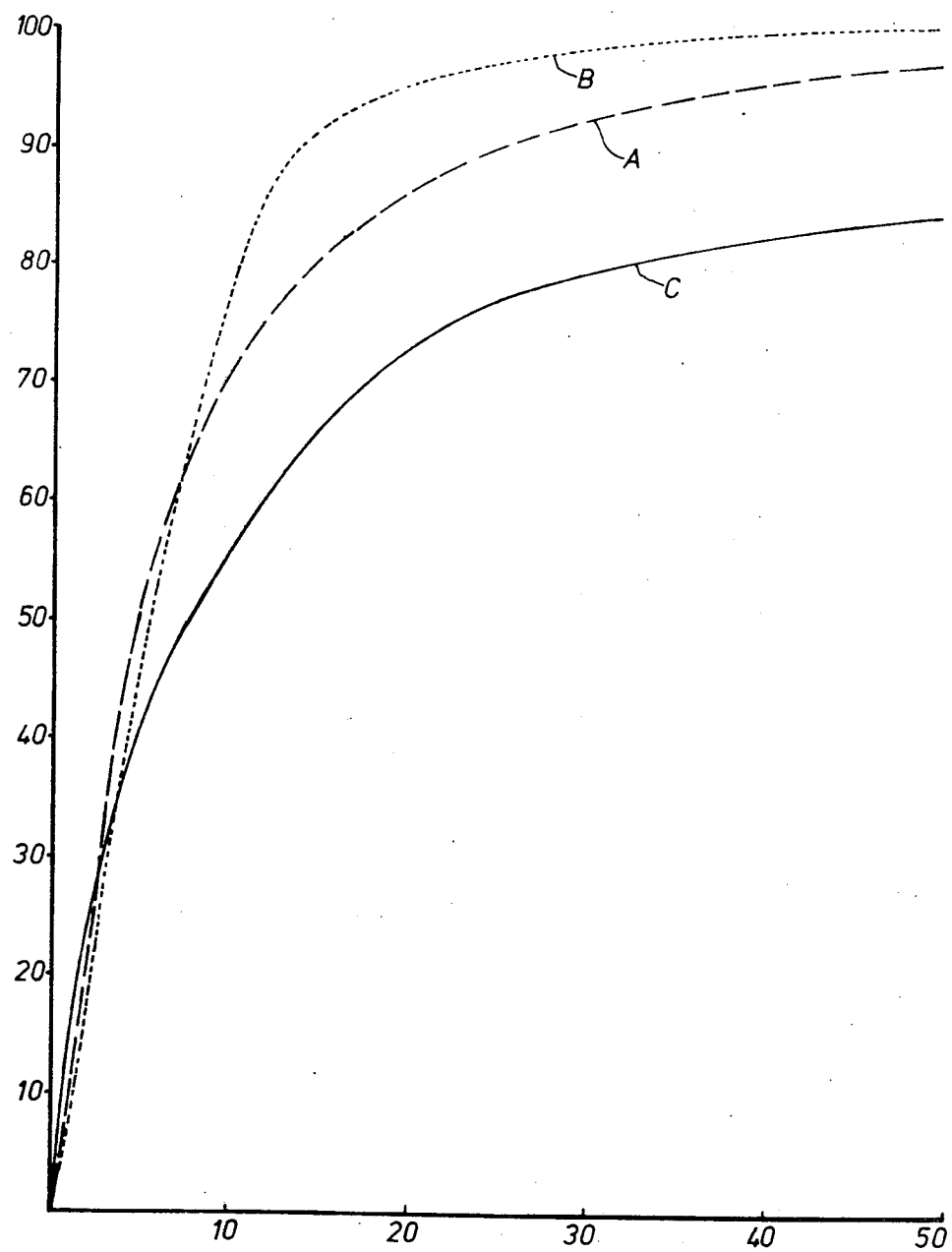

The inhibition values (expressed in percent inhibition) were determined by subtracting the residual activity of elastase, measured after addition of the inhibitor, from the activity of the enzyme control. The inhibition values of some deamino-BPTI derivatives are tabulated in Tables 3 and 4 below. FIG. 2 shows the dependence of the elastase inhibition on the amount of three inhibitors. Other deamino-BPTI derivatives according to the invention show a similar inhibition curve.

The percentage inhibition of 0.25 nkat of pancreas elastase (pig) by a number of deamino-BPTI derivatives, determined by the method of Bieth et al. with a 15 minute pre-incubation of the inhibitor and the enzyme, is shown in FIG. 2, (in this context see also Table 3).

In FIG. 2, curve A relates to the deamino-BPTI derivative according to Example 4, curve B relates to the deamino-BPTI derivative according to Example 3 and curve C relates to the deamino-BPTI derivative according to Example 18 of the present application.

The ordinate in FIG. 2 indicates the inhibition in percent and the abscissa indicates the amount of deamino-BPTI derivative in μg.

Table 3

Percentage inhibition[1]) of 0.25 nkat of pancreas elastase (pig) by various deamino-BPTI derivatives using succinyl-L-alanyl-L-alanyl-L-alanine-p-nitroanilide as the substrate, determined by the method of J. Bieth et al. [Biochem. Med. 11, 350 (1974)] with a 15 minute pre-incubation (+) and without pre-incubation (−) of the enzyme and the inhibitor.

| Diamino-BPTI derivative prepared according to Example | 50 μg + | 50 μg − | 25 μg + | 25 μg − | 12.5 μg + | 12.5 μg − | 5 μg + | 5 μg − | 2.5 μg + | 2.5 μg − |
|---|---|---|---|---|---|---|---|---|---|---|
| Fraction A | 100 | 98 | 98 | 98 | 93 | 90 | 53 | 63 | 35 | 35 |
| Fraction B |  |  |  | 100 |  | 100 |  | 76 |  | 58 |
| Fraction C |  |  |  | 100 |  | 96 |  | 73 |  | 53 |
| Fraction D |  |  |  | 100 |  | 90 |  | 60 |  | 40 |
| Fraction E |  |  |  | 100 |  | 99 |  | 69 |  | 32 |
| Fraction F | 87 | 86 | 64 | 87 | 40 | 74 | 28 | 44 | 10 | 21 |
| Fraction A |  | 100 |  | 92 |  | 70 |  | 55 |  | 31 |
| Fraction B |  | 99 |  | 90 |  | 75 |  | 60 |  | 30 |
| Fraction C |  | 100 |  | 98 |  | 90 |  | 40 |  | 34 |
| Fraction D |  | 100 |  | 95 |  | 85 |  | 70 |  | 52 |
| Fraction E |  | 100 |  | 96 |  | 90 |  | 65 |  | 30 |
| Fraction F |  | 100 |  | 90 |  | 78 |  | 55 |  | 38 |
| 3 | 97 | 95 | 89 | 91 | 69 | 74 | 44 | 47 | 25 | 15 |
| 4 | 97 | 99 | 90 | 92 | 76 | 73 | 50 | 48 | 33 | 38 |
| 5 | 100 | 99 | 95 | 87 | 86 | 77 | 47 | 35 | 25 | 15 |
| 6 |  | 91 |  | 85 |  | 48 |  | 21 |  |  |
| 7 | 97 | 97 | 82 | 90 | 75 | 77 | 44 | 35 |  |  |
| 10 | 100 | 100 | 94 | 92 | 75 | 75 | 37 | 38 | 21 | 20 |
| 11 |  | 93 |  | 85 |  | 58 |  | 17 |  | 10 |
| 13 | 100 | 100 | 96 | 92 | 91 | 72 | 48 | 37 | 29 | 13 |
| 14 | 100 | 99 | 97 | 98 | 87 | 86 | 45 | 40 | 22 | 20 |
| 18 | 84 | 97 | 77 | 70 | 55 | 51 | 42 | 26 | 26 | 19 |
| 21 | 96 | 95 | 90 | 871 | 55 | 44 | 28 | 18 | 15 | 10 |

Table 3-continued

Percentage inhibition[1] of 0.25 nkat of pancreas elastase (pig) by various deamino-BPTI derivatives using succinyl-L-alanyl-L-alanyl-L-alanine-p-nitroanilide as the substrate, determined by the method of J. Bieth et al. [Biochem. Med. 11, 350 (1974)] with a 15 minute pre-incubation (+) and without pre-incubation (−) of the enzyme and the inhibitor.

| Diamino-BPTI derivative prepared according to Example | 50 μg + | 50 μg − | 25 μg + | 25 μg − | 12.5 μg + | 12.5 μg − | 5 μg + | 5 μg − | 2.5 μg + | 2.5 μg − |
|---|---|---|---|---|---|---|---|---|---|---|
| 22 |  | 67 |  | 45 |  | 27 |  | 12 |  | — |

[1] Calculated from: % inhibition = $\left(1 - \dfrac{\Delta \text{OD test}}{\Delta \text{OD enzyme control}}\right) \times 100$

Table 4

Percentage inhibition[1] of 0.25 nkat of pancreas elastase (pig) by several deamino-BPTI derivatives using soluble elastin as the substrate, by the method of S. Keller and I. Mandl [Biochem. Med. 5, 342 (1971)] with a 15 minute pre-incubation (+) or without pre-incubation (−) of the enzyme and the inhibitor.

| Deamino-BPTI derivative prepared according to Example | 50 μg + | 50 μg − | 25 μg + | 25 μg − | 12.5 μg + | 12.5 μg − | 5 μg + | 5 μg − | 2.5 μg + | 2.5 μg − |
|---|---|---|---|---|---|---|---|---|---|---|
| 3 | 97 | 94 | 94 | 88 | 92 | 84 | 59 | 45 | 38 | 20 |
| 4 | 95 | 98 | 94 | 92 | 86 | 82 | 52 | 55 | 46 | 39 |
| 5 |  | 97 |  | 94 |  | 92 |  | 51 |  | 23 |
| 6 |  | 98 |  | 92 |  | 82 |  | 38 |  | 15 |
| 7 | 97 | 98 | 96 | 97 | 89 | 90 | 65 | 50 | 41 | 28 |
| 10 |  | 97 |  | 91 |  | 82 |  | 33 |  | 18 |
| 11 |  | 98 |  | 96 |  | 88 |  | 43 |  | 20 |
| 13 | 97 | 97 | 92 | 93 | 89 | 85 | 59 | 64 | 36 | 31 |
| 14 | 96 | 100 | 88 | 98 | 73 | 84 | 36 | 43 | 18 | 23 |
| 17 | 87 | 81 | 81 | 79 | 75 | 70 | 64 | 53 | 28 | 25 |
| 21 | 96 | 86 | 90 | 84 | 65 | 83 | 54 | 31 | 25 |  |
| 22 |  | 68 |  | 39 |  | 28 |  | 15 |  | — |

[1] Calculated from: % inhibition = $\left(1 - \dfrac{\Delta \text{OD test}}{\Delta \text{OD enzyme control}}\right) \times 100$

(β) Granulocyte-elastase inhibition

The mixture of isoenzymes used for the inhibition tests was obtained from human granulocytes by the method of K. Ohlsson and I. Olsson [Europ. J. Biochem. 42, 519 (1974)]. Succinyl-L-alanyl-L-alanyl-L-alanine-p-nitroanilide [J. Bieth, B. Spiess and C. G. Wermuth, Biochem. Med. 11, 350 (1974)] is particularly suitable as the substrate. The inhibition values of some deamino-BPTI derivatives are recorded in Table 5 below; the dependence of the inhibition on the inhibitor concentrations is given for some derivatives in FIG. 3.

Figure 3:
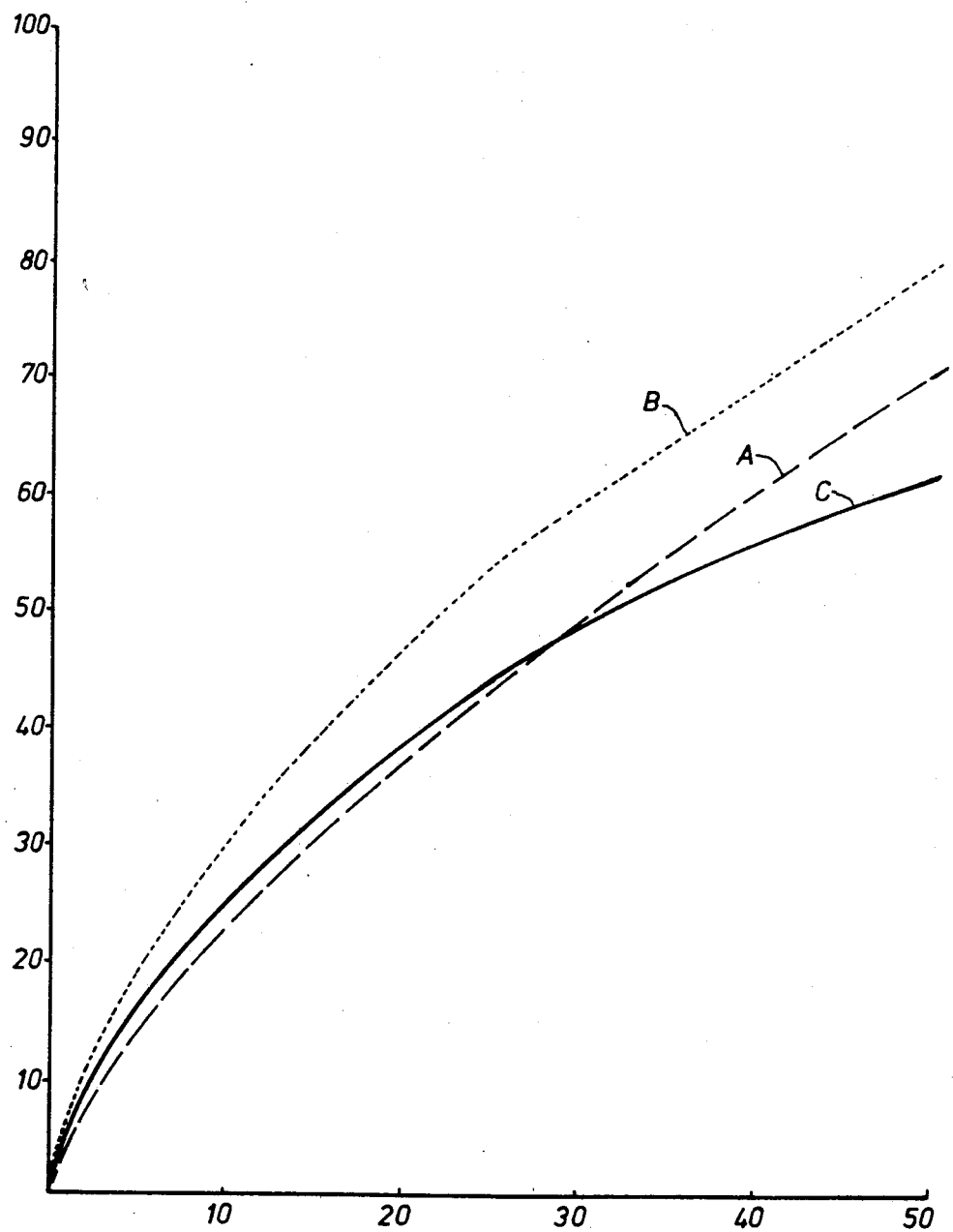

FIG. 3 of the application indicates the percentage inhibition of 0.25 nkat of granulocyte elastase (human) by some deamino-BPTI derivatives, determined by the method of Bieth et al. with a 15 minute pre-incubation of the inhibitor and the enzyme. (In this context compare also Table 5).

The ordinate in FIG. 3 indicates the percentage inhibitory action and the abscissa indicates the amount of deamino-BPTI derivative in μg.

Table 5

Percentage inhibition[1] of 0.25 nkat of granulocyte elastase (human) by various deamino-BPTI derivatives using succinyl-L-alanyl-L-alanyl-L-alanine-p-nitroanilide as the substrate, determined by the method of J. Bieth et al. [Biochem. Med. 11, 350 (1974)] with a 15 minute pre-incubation (+) and without pre-incubation (−) of the enzyme and the inhibitor.

| Deamino-BPTI derivative prepared according to Example | 50 μg + | 50 μg − | 25 μg + | 25 μg − | 12.5 μg + | 12.5 μg − | 5 μg + | 5 μg − |
|---|---|---|---|---|---|---|---|---|
| Fraction A | 88 | 73 | 55 | 60 | 38 | 44 | 17 | 18 |
| Fraction B |  | 83 |  | 49 |  | 35 |  | 20 |
| Fraction C |  | 83 |  | 53 |  | 45 |  | 10 |
| Fraction D |  | 89 |  | 62 |  | 40 |  | 21 |
| Fraction E |  | 78 |  | 48 |  | 35 |  | 9 |
| Fraction F | 55 | 60 | 39 | 42 | 28 | 29 | 6 | 7 |
| Fraction A |  | 58 |  | 38 |  | 15 |  | 8 |
| Fraction B |  | 68 |  | 43 |  | 18 |  | 4 |
| Fraction C |  | 72 |  | 55 |  | 33 |  | 11 |
| Fraction D |  | 76 |  | 55 |  | 23 |  | 6 |
| Fraction E |  | 65 |  | 45 |  | 20 |  | 8 |
| Fraction F |  | 60 |  | 47 |  | 22 |  | 5 |
| 3 | 68 | 71 | 43 | 50 | 23 | 26 | 15 | 10 |
| 4 | 72 | 74 | 43 | 43 | 27 | 33 | 18 | 14 |
| 5 | 72 | 75 | 46 | 45 | 26 | 26 | 13 | 11 |
| 6 |  | 56 |  | 31 |  | 18 |  | 8 |
| 10 | 69 | 66 | 48 | 45 | 27 | 32 | 14 | 14 |
| 13 | 83 | 78 | 55 | 53 | 35 | 22 | 20 | 10 |
| 14 | 81 | 74 | 55 | 44 | 34 | 31 | 19 | 15 |
| 18 | 63 | 61 | 45 | 43 | 28 | 29 | 17 | 16 |
| 21 |  | 53 |  | 29 |  | 20 |  | 9 |

Table 5-continued

Percentage inhibition[1] of 0.25 nkat of granulocyte elastase (human) by various deamino-BPTI derivatives using succinyl-L-alanyl-L-alanyl-L-alanine-p-nitroanilide as the substrate, determined by the method of J. Bieth et al. [Biochem. Med. 11, 350 (1974)] with a 15 minute pre-incubation (+) and without pre-incubation (−) of the enzyme and the inhibitor.

| Deamino-BPTI derivative prepared according to Example | 50 µg + | 50 µg − | 25 µg + | 25 µg − | 12.5 µg + | 12.5 µg − | 5 µg + | 5 µg − |
|---|---|---|---|---|---|---|---|---|
| 22 | 60 | | 46 | | 24 | | 90 | |

[1] Calculated from: $\% \text{ inhibition} = \left(1 - \dfrac{\Delta \text{ OD test}}{\Delta \text{ OD enzyme control}}\right) \times 100$

(b) Chymotrypsin and trypsin inhibition

The activity of chymotrypsin was determined photometrically, using L-tyrosine ethyl ester as the substrate, by the optical test according to H. U. Bergmeyer (Methoden der enzymatischen Analyse (Methods of Enzymatic Analysis), volume 1, page 469, 3rd edition, Verlag Chemie, Wienheim, 1974). The determination of trypsin by the pH-stat method, using benzoyl-L-arginine ethyl ester hydrochloride as the substrate, is given in R. Ruyssen (Symposium on Pharmaceutical Enzymes and their Assay, Universitaire Pers. Ghent, Belgium 1969, page 107). The chymotrypsin and trypsin inhibition was determined as indicated by R. Ruyssen (see above, page 117) for trypsin, using BPTI. The inhibition values (expressed in %) listed in Table 6 below for some deamino-BPTI derivatives were related to the inhibition (= 100%) effected by the same amount of BPTI. The absolute inhibition values were calculated both for BPTI and for deamino-BPTI derivatives, as indicated under "Pancreas elastase inhibition". Table 6 also reports other inhibitory activity which is discussed immediately hereinafter.

isolated by affinity chromatography from the human plasma fraction Cohn-IV-1, by the method of C. Sampaio et al. [Arch. Biochem. Biophys. 165, 133 (1974)]. The inhibition values listed in Table 6 above for some deamino-BPTI derivatives were calculated as indicated under the section "chymotrypsin and trypsin inhibition".

(β) Pancreas kininogenase inhibition

The test enzyme was obtained by the method of C. Kutzbach and G. Schmidt-Kastner [Z. Physiol. Chem. 353, 1099 (1972)] and the activity determinations were carried out by the method given by the same authors (see above). The inhibition values listed in Table 6 above for some deamino-BPTI derivatives were determined as indicated in the section "chymotrypsin and trypsin inhibition".

(d) Plasmin inhibition

The enzymatic activity of plasmin was determined using N-benzoyl-L-phenylalanyl-L-valyl-L-arginine-p-nitroanilide hydrochloride as a substrate. Plasminogen which was activated with urokinase and had been iso-

Table 6

Inhibition of serin protease by some deamino-BPTI derivatives, compared with BPTI

| Designation of the substance BPTI (comparison) | Preparation, described in Examples | Chymotrypsin 100% | Kininogenase pancreas 100% | Kininogenase plasma 100% | Plasmin 100% | Trypsin 100% |
|---|---|---|---|---|---|---|
| Deamino-BPTI derivative, fraction A | | 110 | 4 | 37 | 0 | 10 |
| Deamino-BPTI derivative, fraction B | | 104 | 20 | 37 | 28 | 25 |
| Deamino-BTPI derivative, fraction C | | 73 | 10 | 51 | 0 | 30 |
| Deamino-BPTI derivative, fraction D | 1 | 75 | 25 | 70 | 10 | 30 |
| Deamino-BPTI derivative, fraction E | | 102 | 35 | 45 | 5 | 48 |
| Deamino-BPTI derivative, fraction F | | 44 | 84 | 45 | 5 | 50 |
| Deamino-BPTI derivative, fraction A | | 12 | 10 | 57 | 0 | 10 |
| Deamino-BPTI derivative, fraction B | | 80 | 10 | 31 | 10 | 10 |
| Deamino-BPTI derivative, fraction C | 2 | 72 | 12 | 45 | 36 | 26 |
| Deamino-BPTI derivative, fraction D | | 78 | 10 | 46 | 23 | 15 |
| Deamino-BPTI derivative, fraction E | | 83 | 10 | 49 | 0 | 20 |
| Deamino-BPTI derivative, fraction F | | 96 | 86 | 96 | 36 | 60 |
| Deamino-BPTI derivative | 3 | 93 | 38 | 62 | 93 | 39 |
| Deamino-BPTI derivative | 4 | 10 | 54 | 71 | 86 | 40 |
| Deamino-BPTI derivative | 6 | 95 | 50 | 81 | 86 | 31 |
| Deamino-BPTI derivative | 10 | 56 | 5 | 10 | 86 | 23 |
| Deamino-BPTI derivative | 11 | 87 | 18 | 48 | 86 | 15 |
| Deamino-BPTI derivative | 13 | 116 | 31 | 81 | 86 | 23 |
| Deamino-BPTI derivative | 14 | 78 | 108 | 21 | 86 | 99 |
| Deamino-BPTI derivative | 18 | 84 | 152 | 121 | 95 | 70 |
| Deamino-BPTI derivative | 21 | 145 | 57 | 52 | 86 | 54 |
| Deamino-BPTI derivative | 22 | 102 | 80 | 127 | 86 | 80 |

(c) Kininogenase inhibition

(a) Plasma kininogenase inhibition

The kininogenase activity was determined by the pH-stat method, according to C. Sampaio, S. C. Wong and E. Shaw [Arch. Biochem. Biophys. 165, 133 (1974)], but, because of the higher rate of hydrolysis, benzoyl-L-arginine ethyl ester hydrochloride was used as the substrate in place of tosyl-L-arginine methyl ester hydrochloride. The mixture of the isoenzymes was lated from human plasma by means of affinity chromatography [D. G. Deutsch, E. T. Mertz, J. Med. 3, 224 (1972)] was used as the enzyme. (The substrate is marketed by AB Bofors, Nobel Division, Mölndal, Sweden under the designation S 2160).

The test instructions were taken from Svendsen and Amundsen (Abstract of a paper read at IVth Congress of the International Society of Thrombosis and Haemostasis, Vienna, June 1973), with slight modifications: for each determination, two parallel test tubes (A and B), each containing 0.3 CU "casein units" according to J. T. Sgouris, Vox. Sang. 5, 357 (1960) of plasmin, dissolved in 1.0 ml of a buffer (0.1 M tris-(hydroxymethyl)-aminomethane HCl/0.05 M NaCl, pH 7.2), are prepared. In order to determine their inhibitory activity, BPTI and deamino BPTI derivatives are dissolved in the said buffer to give a concentration of 50 µg/ml; 1.0 ml of the solutions is added to the plasmin, 1.0 ml of the said buffer is added to the test tubes for the determination of the full plasmin activity. All the test tubes are incubated for 10 minutes at 20° C., 0.25 ml of a $10^{-3}$ M aqueous solution of S 2160 is added to one of the parallel test tubes (A) and first 0.25 ml of glacial acetic acid and then 0.25 ml of the solution of S 2160 are added to the other test tubes (B). After incubation for 30 minutes at 20° C., 0.25 ml of glacial acetic acid is added to test tubes A also.

The p-nitroaniline liberated by the enzyme is determined by photometric determination of the difference in the extinctions at 405 nm in the test tubes A and B.

If the difference in extinction which is caused by plasmin on its own is designated $\Delta E_{100}$ and the difference in extinction measured in the presence of inhibitors is designated $\Delta E$, the inhibition of the plasmin by the inhibitors, under the indicated conditions, is calculated by the following expression:

$$\frac{\Delta E_{100} - \Delta E}{\Delta E_{100}} \times 100\%$$

Table 6 above gives the inhibition values which were determined in this way and were obtained with 50 µg of derivative per 0.3 CU of plasmin, for some deamino-BPTI derivatives. In contrast to the values given for the other enzymes shown in Table 6, these values were not correlated to BPTI. 0.6 µg of BPTI already gives 50% inhibition of 0.3 CU of plasmin.

(e) Cathepsin-G inhibition

The enzyme was isolated by the method of W. Schmidt and K. Havemann [Z. Physiol. Chem. 355, 1077 (1974)]. The inhibition tests were carried out with acetyl-L-tyrosine ethyl ester, as described by A. Vandermeers et al. [J. Clin. Chem. 18, 1514 (1972)].

5. Inflammation-inhibiting action (a) Carrageenan-induced inflammatory reaction

The inflammatory reaction was induced by intraplantary injection of 0.1 ml of a 0.5% solution of carrageenan (carrageenan, Marine Colloids, Inc., New York) in a back paw of Wistar rats weighing 130–160 g. The deamino-BPTI derivatives according to the invention and also BPTI which were used for the treatment of the inflammatory reaction, were dissolved in 0.9% sodium chloride solution in a concentration of 10–20 mg/ml. The test animals were treated by intraperitoneal, intramuscular, subcutaneous or intravenous injection of 0.5–1.0 ml of a solution of deamino-BPTI derivatives and, for comparison, of BPTI, either prophylactically, that is to say before setting of the inflammation noxa, or therapeutically, that is to say after setting of the inflammation noxa. The swelling of the inflamed paw, which is a measure of the severity of the inflammatory reaction, was followed, as a function of time, using the KEMPER antiphlogmeter [F. Kemper and G. Ameln, Z. Ges. exp. Med. 131, 407–411 (1959)].

The value measured 4 hours after setting of the inflammation noxa was used to determine the relationships between the dose and the effect. The result of the comparison of a deamino-BPTI derivative according to Example 3 with BPTI is given in Table 7 below. The doses, in mg/kg, which effect a 10% ($ED_{10}$), 30% ($ED_{30}$) and 50% ($ED_{50}$) inhibition of the swelling of the paw, compared with the untreated control group, are given.

Table 7

Inhibition of the carrageenan-induced inflammatory reaction in a rat's paw by intravenous treatment with BPTI and the deamino-BPTI derivative according to Example 3.

(The treatment was carried out 15 minutes after setting of the inflammation noxa. The average values and the 5% confidence limits (in brackets) are recorded).

| Designation of the substance | Obtained according to Example | $ED_{10}$ mg/kg | $ED_{30}$ mg/kg | $ED_{50}$ mg/kg |
|---|---|---|---|---|
| BPTI | | 7.0 (5.9–7.8) | 12.7 (11.7–13.6) | 22.8 (20.8–26.1) |
| deamino-BPTI derivative | 3 | 0.07 (0.03–0.14) | 0.5 (0.3–0.8) | 3.9 (3.1–5.1) |

(b) Kaolin-induced inflammatory reaction

The inflammatory reaction was induced by intraplantary injection of 0.1 ml of a 10% kaolin suspension (Bolus white, finely powdered, Merck A. G., Darmstadt) in a back paw of Wistar rats weighing 130–160 g. The substances were tested, and the results were evaluated, as indicated under (a), and reported in Table 8 below.

Table 8

Inhibition of the kaolin-induced inflammatory reaction in a rat's paw by intravenous treatment with BPTI and the deamino-BPTI derivatives according to Examples 3 and 18.

(The treatment was carried out 15 minutes after setting of the inflammation noxa. The average values and the 5% confidence limits (in brackets) are recorded.)

| Designation of the substance | Obtained according to Example | $ED_{10}$ mg/kg | $ED_{30}$ mg/kg | $ED_{50}$ mg/kg |
|---|---|---|---|---|
| BPTI | | 9.1 (5.2–12.3) | 17.6 (13.7–22.1) | 33.9 (26.7–52.1) |
| deamino-BPTI derivative | 3 | 7.2 (0.02–0.71) | 36.5 (5.9–9.1) | (26.7–55.4) |
| deamino-BPTI derivative | 18 | 0.6 (0.12–1.4) | 2.7 (1.1–4.4) | 11.7 (8.8–15.6) |

A comparison of the action of the deamino-BPTI derivatives according to Examples 3 and 18 shows that, in respect of their inflammation-inhibiting action, they are superior to BPTI.

Figure 5:
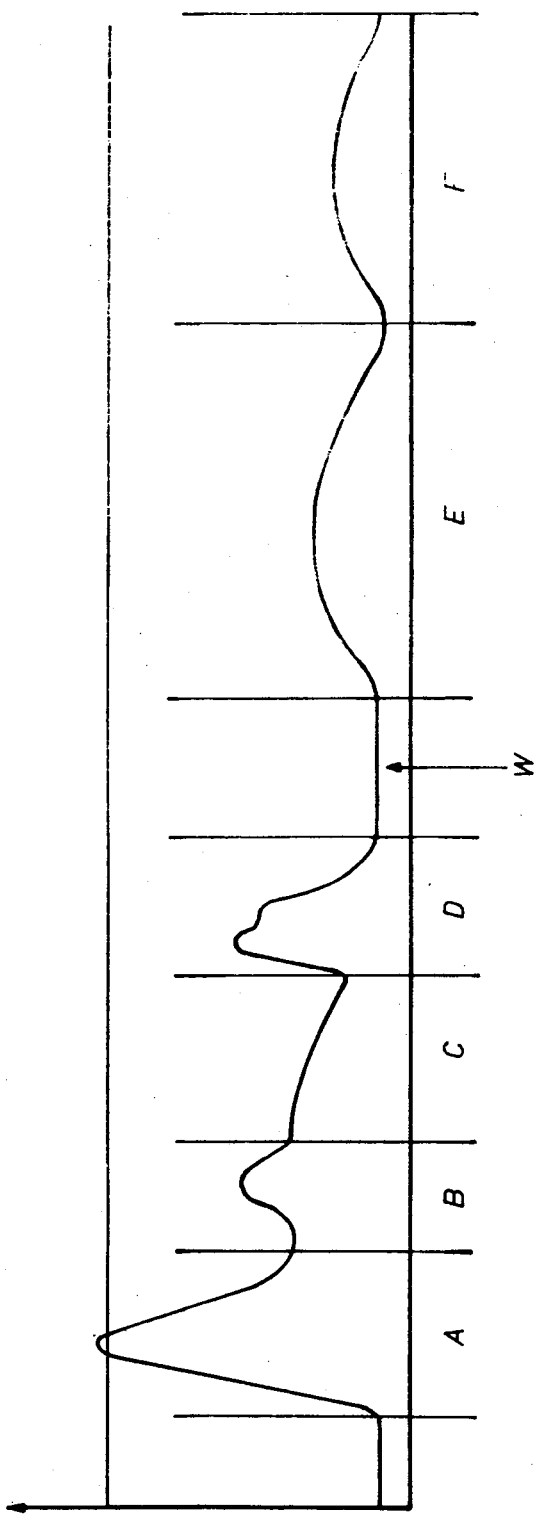

The superiority of the deamino-BPTI derivatives as medicaments, compared with BPTI, can also be seen from the finding that BPTI displays inflammation-inhibiting actions in the kaolin-induced inflammatory reaction only when it is administered prior to, or up to 30 minutes after, setting of the inflammation noxa, while the deamino-BPTI derivatives are also effective at later times after setting of the inflammation noxa (FIG. 5).

(c) Aerosil-induced inflammatory reaction

The inflammatory reaction was induced by intraplantary injection of 0.1 ml of a 2% aerosil suspension (Aerosil 200, Dugussa AG, Frankfurt) in a back paw of Wister rats weighing 130-160 g. The deamino-BPTI derivatives according to the invention, and the BPTI, used for treatment of the inflammatory reaction were dissolved in 0.9% sodium chloride solution in a concentration of 10-20 mg/ml. The test animals were treated by intraperitoneal, subcutaneous or intravenous injection of 0.5-1.0 ml of a solution of deamino-BPTI derivatives and, for comparison, of BPTI, 15 hours after setting of the inflammation noxa. The swelling of the inflamed paw, which is a measure of the severity of the inflammatory reaction, was followed, as a function of time, using the KEMPER antiphlogmeter. In order to ascertain the relationships between the dose and the effect, the value obtained 21 hours after the induction of inflammation (= 6 hours after injection of the deamino-BPTI derivatives according to the invention or of BPTI) was determined. The result of the comparison of the deamino-BPTI derivatives according to Example 3 and 18 with BPTI is given in Table 9 below. The doses, in mg/kg, which effect a 10% ($ED_{10}$), 15% ($ED_{15}$) and 30% ($ED_{30}$) inhibition of the swelling of the paw, compared with the untreated control groups, are given.

Table 9

Inhibition of the aerosil-induced inflammatory reaction in a rat's paw by intravenous treatment with BPTI and the BPTI derivatives according to Example 3 and 18.
(Treatment was carried out 15 hours after setting of the inflammation noxa. The average values and the 5% confidence limits are recorded.)

| Designation of the substance | Obtained according to Example | $ED_{10}$ mg/kg | $ED_{15}$ mg/kg | $ED_{30}$ mg/kg |
|---|---|---|---|---|
| BPTI | | NO INHIBITION DETECTABLE | | |
| deamino-BPTI derivative | 3 | 2.0 (0.1–4.6) | 4.9 (1–8.5) | 61.5 (32–500) |
| deamino-BPTI derivative | 18 | 5.1 (3.7–6.4) | 6.3 (4.8–7.6) | 11.4 (9.6–13.4) |

Figure 4A:
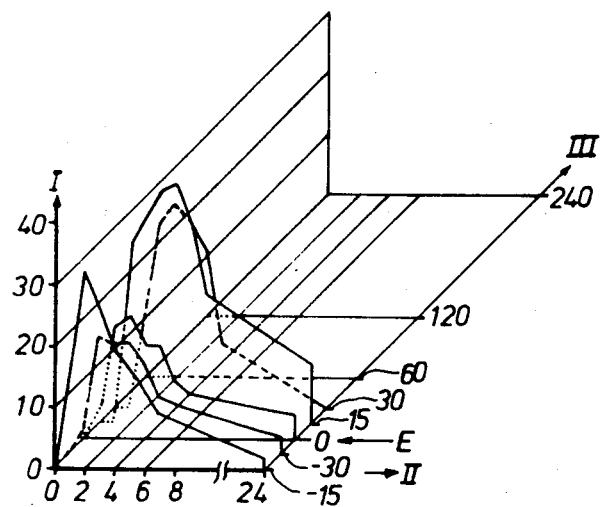
Figure 4B:
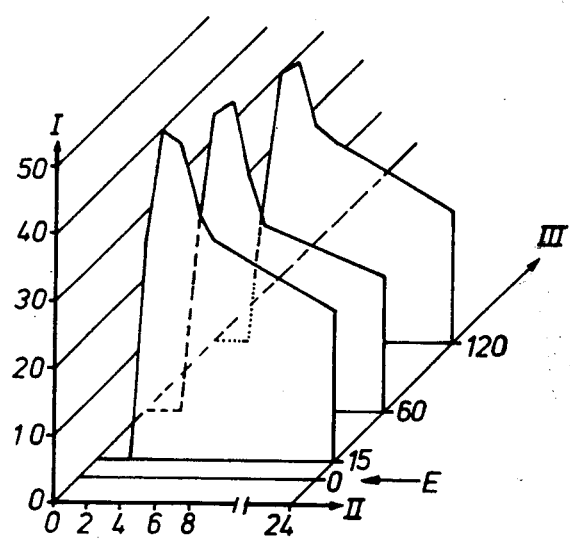

A comparison of the inflammation-inhibiting action of BPTI (A) and of the deamino-BPTI derivative according to Example 3 (B) in the kaolin-induced inflammation of a rat's paw after intravenous administration of 20 mg of inhibitor / kg of body weight at different times before and after setting of the inflammation noxa can be taken from FIGS. 4 A and 4 B.

In FIG. 4 A, BPTI was administered 30 and 15 minutes before, at the same time as and 15, 30, 60, 120 and 240 minutes after induction of inflammation. In FIG. 4 B, the deamino-BPTI derivative according to Example 3 was administered 15, 60 and 120 minutes after setting of the inflammation noxa (induction of inflammation).

The figures on the three axes I, II and III indicate the following:

I: Inhibition of the swelling of the paw, in percent
II: Number of hours after the induction of inflammation
III: Number of minutes before/or after administration of BPTI (FIG. 4 A) or the number of minutes after administration of the deamino-BPTI derivative according to Example 3 (FIG. 4 B). E = time at which inflammation is induced.

The result of the therapy experiments with the deamino-BPTI derivatives according to Example 3 and 18 (Table 9) shows the effectiveness of the deamino-BPTI derivatives used in this experimental model, in which BPTI, in the same dosage, does not inhibit the inflammatory reaction. The superiority of deamino-BPTI derivatives as medicaments, compared with BPTI, is thus demonstrated. This result is in accord with the results obtained from the experiments with the kaolin model (b), in which the therapeutic superiority is again shown by the inflammation-inhibiting action at a later time after setting of the inflammation noxa.

Because of their biological activity, the new deamino derivatives, according to the invention, of the kallikreintryps in inhibitor obtained from cattle organs (BPTI) can be employed, in particular, for the treatment of the following diseases and disease symptoms in humans and animals:

1. Various forms of shock and post-traumatic and postoperative complications,
2. disorders in blood clotting,
3. acute and chronic inflammatory reactions, especially for the therapy and prophylaxis of damage to organs, such as, for example, pancreatitis and radiation-induced enteritis and inflammatory reactions caused by immune complexes, such as immune-vasculitis, glomerulonephritis and arthritides; collagenoses and especially rheumatoid arthritis,
4. arthritides caused by deposits due to metabolic processes (for example gout),
5. degeneration of the elastic components of the connective tissue parts of organs, such as in the case of arteriosclerosis, and
6. radiation-induced enteritis.

The present invention also includes pharmaceutical compositions, which comprise a deamino derivative of BPTI as hereinabove described as the active ingredient in combination with a pharmaceutically acceptable, nontoxic inert diluent or carrier.

The pharmaceutical compositions of the present invention contain a major or minor amount, e.g. 99.5% to 0.1%, preferably 95% to 0.5%, of at least one deamino derivative of BPTI of the present invention in combination with a pharmaceutically acceptable, nontoxic, inert diluent or carrier, the carrier comprising one or more solid, semisolid or liquid diluents, filler and formulation adjuvant which is nontoxic, inert and pharmaceutically acceptable. Solutions or suspensions will generally contain from about 0.01 to 100 mg/ml of the deamino derivative of BPTI, preferably from about 0.01 to about 10 mg/ml. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, 3 or 4 times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from about 0.1 to about 20 mg of the deamino derivative of BPTI per kg. of body weight and preferably from about 1 to about 10 mg/kg of body weight, per day. In some instances a sufficient therapeutic effect can be obtained at a lower dose while in others, a larger dose will be required.

The deamino derivatives of BPTI of the invention are administered and formulated as the known BPTI. Preferred formulations include:

1. Solutions for parenteral applications, e.g. for intravenous, intramuscular, subcutaneous injection or intraarticular and intratumoral administration.
2. Solutions for continuous intravenous infusion.
3. Solutions for application as aerosols for inhalation.
4. Solutions, emulsions, ointments, pastes, gels, creams, sprays, lotions, powders for external local application.
5. Solutions and tablets for oral administration.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alignate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular, intravenous or intratumoral injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, and the like. Other excipients such as emulsifiers, preservatives, colorants, perfumes and the like can also be present.

The deamino derivative of BPTI can also be administered as an aerosol, utilizing the usual propellants such as the chlorohydrocarbons.

The following Examples illustrate the preparation of representative deamino derivatives of BPTI according to the invention.

EXAMPLE 1

500 mg (77 $\mu$mols) of BPTI were dissolved in 200 ml of ice-cold, oxygen-free 0.25 M acetic acid. 50 ml of 2M sodium nitrite solution were added dropwise, at 0°–4° C. in the course of 30 minutes to the solution of the inhibitor, while passing nitrogen through the mixture and stirring well, and the reaction mixture was finally kept under a nitrogen atmosphere at +4° C. for 24 hours. During this period, the pH value of the solution rose from 3.7 to 4.1

The reaction mixture was concentrated by ultrafiltration in an ultrafiltration cell (Amicon) with the aid of a 05 Diaflow-UM membrane, diluted with water and concentrated again. This procedure was repeated several times which resulted in a partial precipitation of the reaction product 0.1 M ammonium hydroxide solution was added to the residual mixture until the precipitate had largely gone into solution, the pH value of the solution was adjusted to 6.8 by adding 0.1 M acetic acid and water was added in an amount such that the concentration of ammonium acetate reached 0.05 M. A small amount of undissolved material was separated off by centrifuging and the supernatant solution was chromatographed in a SP-Sephadex ® C-25 column (2.5 × 80 cm) equilibrated with 0.05 M ammonium acetate solution of pH 6.8. (Sephadex ® = crosslinked dextran). The column was first eluted with 500 ml of 0.05 M ammonium acetate solution of pH 6.8 and then with 500 ml of 0.5 M ammonium acetate solution of the same pH value. The elution profile is shown in FIG. 5. The individual fractions A to F (compare FIG. 5) were freeze-dried and the lyophilisates were freed from salts, in some cases by chromatography on Biogel P 2 using 0.1 M ammonium hydroxide as the eluant and in some cases by ultrafiltration. The yields and spectroscopic data of the preparations obtained from the individual fractions are compiled in Table 10 below.

Table 10

Fractionation, on SP-Sephadex ® C-25, of the deamino-BPTI mixture prepared according to Example 1 (compare FIG. 6).

| Fraction No. | Designation | Amount (mg) | $E \frac{280 \text{ nm}}{425 \text{ nm}}$ |
|---|---|---|---|
| 21 – 30 | A | 224 | 5.53 |
| 31 – 40 | B | 73 | 8.57 |
| 41 – 52 | C | 37 | 6.15 |
| 53 – 63 | D | 87 | 4.61 |
| 75 – 105 | E | 67 | 16.60 |
| 106 – 140 | F | 12 | 13.25 |

The results of the quantitative amino-acid analyses are given in Table 2. In FIG. 5, the extinction, in percent is given on the ordinate and the designation of the particular fraction A to F is given on the abscissa. At point W the eluant is changed (0.5 ammonium acetate solution in place of 0.05 M ammonium acetate solution).

EXAMPLE 2

500 ml of BPTI were reacted with sodium nitrite in a solution containing acetic acid, as described in Example 1. After 24 hours the pH value was adjusted to 9.0 by adding concentrated aqueous ammonia and, as described in Example 1, the solution was freed from salts by ultrafiltration. Constituents of higher molecular weight were separated off by chromatography in a Sephadex ® G-50 column (2.5 × 100 cm) using 0.1 M ammonia solution. After freeze-drying, the residue was dissolved in 10 ml of 0.1 M aqueous ammonia and the pH of the solution was adjusted to 6.8 with 0.1 M acetic acid. The clear solution was now applied, as indicated in Example 1, to a SP-Sephadex ® C-25 column (2.5 × 70 cm) and eluted first with 500 ml of 0.05 M ammonium acetate solution of pH 6.8, followed by 500 ml of 0.5 M ammonium acetate solution of pH 6.8 and finally with 200 ml of 0.1 M aqueous ammonia. The elution profile is comparable with that obtained according to Example 1. The yields and spectroscopic data for the individual fractions are given in Table 11 below.

Table 11

Fractionation, on SP-Sephadex ® C-25, of the deamino-BPTI mixture prepared according to Example 2.

| Fraction No. | Designation | Amount (mg) | $E \frac{280 \text{ nm}}{425 \text{ nm}}$ |
|---|---|---|---|
| 19 – 27 | A | 7 | 9.0 |
| 28 – 42 | B | 22 | 13.3 |
| 43 – 48 | C | 177 | 17.4 |
| 49 – 51 | D | 44 | 21.2 |
| 52 – 59 | E | 9 | 15.5 |
| 113 – 127 | F | 185 | 22.1 |

EXAMPLE 3

2 g of BPTI were deaminated, as described in Example 2. After concentrating the reaction solution by ultrafiltration, the residual mixture was freed from salts in a Biogel P-2 column using 0.1 M aqueous ammonia as the eluant. The residue obtained after freeze-drying was chromatographed on Sephadex ® G-50, using 0.1 M acetic acid as the eluant, in order to separate off reaction products (about 5%) of higher molecular weight. 1.6–1.72 g (80–85%) of substance were obtained.

EXAMPLE 4

500 mg of BPTI were reacted in 200 ml of 0.25 M acetic acid, which at the same time was 8 M in respect of urea, with sodium nitrite, as described in Example 2. After a reaction time of 20 hours, the reaction mixture was concentrated to 30 ml by ultrafiltration and the residual mixture was gelfiltered in a Sephadex ® G-10 column (2.5 × 150 cm) using 0.1 M aqueous ammonia as the eluant, in order to separate off the urea. The fraction eluted immediately after the void volume was lyophilised and then chromatographed on Sephadex ® G-50 using 0.2 M acetic acid as the eluant. After freeze-drying, 40 mg (8%) of substance a higher molecular weight were obtained from the first fraction and 392 mg (79%) of a colourless substance were obtained from the second fraction.

EXAMPLE 5

500 mg of BPTI were reacted in a mixture of 195 ml of water and 5.7 g of trifluoroacetic acid with sodium nitrite, in the manner described in Example 2. After the nitrite solution had been added dropwise, the pH value had risen from 1.65 to 3.43. The reaction mixture was stirred at +4° C. for 20 hours and the pH value was adjusted to 8.8 with concentrated ammonium solution before the mixture was concentrated. The concentrated solution was freed from salts via Sephadex ® G-10. Substances of higher molecular weight were then separated off by chromatography on Sephadex ® G-50. 360 mg (72%) of a residue were obtained by lyophilising the main fraction.

EXAMPLE 6

500 mg of BPTI were reacted, following the procedure of Example 4, in 200 ml of 0.25 M acetic acid, which at the same time was 3 M in respect of guanidine hydrochloride. During the reaction the pH value of the solution rose from 2.86 via 3.86 to 3.96. After the customary working up, 320 mg (64%) of a lyophilisate were obtained.

EXAMPLE 7

200 mg (30.8 μmols) of BPTI were dissolved, as indicated in Example 2, in 90 ml of 0.25 M acetic acid and 4.7 ml (40 mmols) of isoamyl nitrite were added dropwise, at 4° C., while stirring and passing nitrogen over the mixture. After 20 hours the reaction mixture was worked up in the manner described in the preceding examples. The yield of lyophilisate was 168 mg (84%).

EXAMPLE 8

Following the general procedure of Example 2, 200 mg (30.8 μmols) of BPTI were dissolved in 90 ml of 0.5 M sodium acetate buffer of pH 5.1 g (40 mmols) of nitrosylsulphuric acid were introduced in a total of 4 portions at intervals of 10 minutes, at +4° C., in a $N_2$ atmosphere and while stirring well. The mixture was stirred for a further 5 hours at +4° C. and the pH value of the reaction mixture (1.25) was adjusted to 9.8 by adding concentrated ammonium hydroxide solution. The mixture was worked up in the manner described in the preceding examples. The yield of lyophilisate was 158 mg (79%).

EXAMPLE 9

200 mg (30.8 μmols) of BPTI were dissolved in a mixture of 72 ml of absolute dimethylsulphoxide, 8 ml of water and 1.35 ml of glacial acetic acid. The solution was cooled to +4° C. and a solution of 2.76 g (40 mmols) of sodium nitrite in 16 ml of dimethylsulphoxide and 4 ml of water was added in the course of 30 minutes, while stirring well with a magnetic stirrer and passing nitrogen into the mixture. The reaction mixture was stirred at +4° C. for 20 hours. The dimethylsulphoxide and the salts were separated off by gel filtration of the reaction mixture through Sephadex ® G-10 (column 5 × 100 cm) using 0.1 M ammonium hydroxide solution as the eluant. The fraction containing protein was freeze-dried. 108 mg (54%) of residue were obtained from the main fraction on Sephadex ® G-50 using 0.1 M aqueous ammonia as the eluant. The quotient of the UV extinctions at 280 nm and 425 nm was 1.72 for this preparation. It follows from this that 2-tyrosine residues in the molecule of the derivative have been nitrated.

EXAMPLE 10

500 mg (77 μmols) of BPTI were dissolved in 200 ml of a 0.5 M sodium nitrate solution. The pH value of the solution was adjusted to 3.5 with 2 N hydrochloric acid, at +4° C., while passing nitrogen through the solution and while stirring well with a magnetic stirrer, and was kept constant for 24 hours. The pH value was then adjusted to 8.8 by adding concentrated ammonium hydroxide solution and the volume of the reaction solution was concentrated to about 20 ml by ultrafiltration through a UM-2 filter. The concentrated solution was freed from salts by gel filtration through Sephadex ® G-10. After the eluates containing protein had been freeze-dried, the residue was chromatographed on Sephadex ® G-50 using 0.1 M acetic acid as the eluant. 390 mg (78%) of substance were isolated from the main fraction by freeze-drying. In addition 48 mg (about 10%) of substances of higher molecular weight were obtained.

EXAMPLE 11

500 mg (77 μmols) of BPTI were dissolved, as described in Example 2, in 200 ml of 0.25 M acetic acid. After adding 282 mg (3 mmols) of phenol to the solution, 50 ml of a 2 M sodium nitrite solution were added dropwise in the course of 1 hour at 4° C., while stirring and passing nitrogen through the mixture. During the addition the reaction solution developed a yellow coloration. The mixture was kept at +4° C. for 17 hours and the pH value of the solution was then adjusted to 8.5 with concentrated ammonium hydroxide solution. The deep yellow solution then developed a redbrown coloration. The reaction mixture was concentrated by ultrafiltration in the customary manner to a volume of about 50 ml and the residual mixture was applied to a Sephadex ® G-10 column (5 × 100 cm). The mixture was eluted with 0.1 M ammonium hydroxide solution in order to separate off the salts and the by-products derived from phenol. The lyophilisate obtained from those protein-containing fractions which were eluted immediately after the void volume was now dissolved in 0.1 M acetic acid and the solution was rechromatographed on Sephadex ® G-50 using 0.1 M acetic acid as the eluant, in order to separate off substances of higher molecular weight. 335 mg (67%) of lyophilisate were obtained from the main fraction.

EXAMPLE 12

5.1 g (40 mmols) of nitrosylsulphuric acid were added in 4 portions to 200 mg of BPTI in 100 ml of 1 M sodium acetate buffer of pH 5.3, as described in Example 8. When the additions were made the pH value fell via 4.0 and 2.9 to, ultimately, 1.7. After 10 minutes the pH value of the solution was adjusted to 3.25 and the solution was stirred for 20 hours at +4° C. Ammonia was then added to the reaction mixture until a pH value of 8.5 was obtained and the solution was freed from salts via Sephadex ® G-10 using 0.1 M ammonium hydroxide solution as the eluant. The substance obtained after freeze-drying was chromatographed on Sephadex ® G-50, using 0.1 M acetic acid as the eluant, in order to separate off the polymeric substances. On freeze-drying, the main fraction gave 166 mg (83%) of substance.

EXAMPLE 13

200 mg of mononitro-BPTI [obtained by the method of B. Meloun, I. Frič and F. Sörm, Europ. J. Biochemistry 4, 112 (1968)] were dissolved in 80 ml of 0.25 M acetic acid and reacted, at +4° C., under nitrogen, with 20 ml of a 2 M aqueous solution of sodium nitrite, as described in Example 2, and after stirring for 20 hours at +4° C., again as described in Example 2, the reaction mixture was worked up. After the reaction product, which had been freed from salts and purified by chromatography on Sephadex ® G-50, had been freeze-dried, 150 mg (75%) of a yellowish lyophilisate were obtained.

EXAMPLE 14

500 mg of dinitro-BPTI (obtained according to the method of B. Meloun et al. (see Example 12) were dissolved in 200 ml of 0.25 M acetic acid and 50 ml of 2 M sodium nitrite solution were added in the course of one hour, at +4° C., in a stream of nitrogen. The reaction solution was stirred at +4° C. for 24 hours. During this time, solid constituents precipitated and these were dissolved completely by adjusting the pH value to 9.2 with ammonium hydroxide solution. After concentrating the solution by ultrafiltration, the residual mixture was freed from salts by gel filtration through Biogel P-2. Substances of higher molecular weight were separated off by chromatography on Sephadex ® G-50 using 0.1 M acetic acid as the eluant. After lyophilising, 470 mg (94%) of a yellow substance were obtained.

EXAMPLE 15

430 mg of the deamino-dinitro-BPTI derivative obtained according to Example 14 were dissolved in 8 ml of 0.1 M tris(hydroxymethyl)-aminomethane hydrochloride buffer of pH 7.5. 300 mg of sodium dithionite were added to this solution in 2 portions at intervals of 10 minutes, at +4° C., while stirring well. After a further 10 minutes, the reaction mixture was freed from salts by gel filtration through Sephadex ® G-10 and the protein fraction was isolated by freeze-drying. The substance was dissolved in 10 ml of 0.1 M acetic acid and the solution was chromatographed on Sephadex ® G-50. 320 mg (75%) of a colourless substance were obtained from the main fraction by lyophilising. A further 50 mg (12%) of substances of higher molecular weight were obtained from a previous fraction containing protein.

EXAMPLE 16

500 mg of BPTI were dissolved in 200 ml of 0.25 M acetic acid, as described in Example 2. 2.95 g (50 mmols) of acetamide were added to the solution and 50 ml of a 2 M sodium nitrite solution were added dropwise at +4° C. After stirring for 20 hours at +4° C., the pH value of the reaction solution was adjusted to 9.0 with aqueous ammonia and the volume was reduced to 50 ml by ultrafiltration. The residual mixture was freed from salts by gel filtration through Sephadex ® G-10, using 0.1 M aqueous ammonia as the eluant. The lyophilisate obtained from the fraction containing protein was dissolved in 0.1 M acetic acid and chromatographed on Sephadex ® G-50 using 0.1 M acetic acid as the eluant. Lyophilising gave a main fraction of 418 mg (84%), in addition of 35 mg (7%) of substances of higher molecular weight.

EXAMPLE 17

200 mg of BPTI were dissolved in 100 ml of 0.25 M acetic acid and, after adding 1.51 g (12.5 mmols) of dimethylaniline to the solution, were reacted with sodium nitrite solution, as described in Example 11. After adjusting the pH value to 8.5 with concentrated aqueous ammonia, the reaction mixture was freed from salts by filtration through Sephadex ® G-10. The substance isolated after freeze-drying the fraction containing protein was dissolved in 0.1 M acetic acid and the solution was chromatographed on Sephadex ® G-50, using 0.1 M acetic acid as the eluant. After freeze-drying, 146 mg (73%) of residue were obtained from the main fraction. A further 20 mg (10%) of substance were isolated from the high molecular weight fraction.

EXAMPLE 18

27 mg (0.31 mmols) of 5-aminotetrazole-(1,H) [J. Thiele, Liebigs Ann. Chem. 270, 1 (1892)] were dissolved in 5 ml of 1 M hydrochloric acid. 25 mg (0.35 mmol) of solid sodium nitrite were added to this solution at +4° C., while stirring with a magnetic stirrer. After stirring for 10 minutes, a small amount of urea was added. After a further 10 minutes, 4 ml of ice-cold sodium hydroxide solution (1 M) were added. The solution thus obtained was added to a solution of 1 g (0.154 mmol) of BPTI in 10 ml of 1 M potassium bicarbonate/sodium carbonate buffer of pH 9.4, while stirring well. The reaction mixture was stirred at +4° C. for 10 minutes, a small amount of phenol was added and finally the pH value was brought to 5.5 with glacial acetic acid. The slightly coloured solution was freed from salts by gel filtration through a Sephadex ® G-10 column (2.2 × 90 cm), using 0.1 M acetic acid as the eluant. After lyophilising the fractions containing protein, 110 mg (11%) of impurities of higher molecular weight were separated off by chromatography on Sephadex ® G-50 using 0.1 M acetic acid as the eluant. When the main fraction was freeze-dried, 660 mg (~66%) of residue were obtained. The absorption spectrum (from 250–600 nm) is given in FIG. 1.

EXAMPLE 19

As described in Example 18, the diazonium salt was prepared from 27 mg of aminotetrazole in 5 ml of 1 M hydrochloric acid using a solution of 25 mg of sodium nitrite in 0.3 ml of water and excess nitrite was destroyed by reaction with 15 mg of urea. The solution of the diazonium salt was combined with a solution of 1 g of BPTI in 10 ml of water. 4 N sodium hydroxide solution was added, while cooling well, until a pH value of 4.5 was reached and the mixture was stirred for 45 minutes, while cooling. Acetic acid was then added and the solution was freed from salts on Sephadex ® G 10, and chromatographed, according to Example 18. Ultimately 856 mg (86%) of substance were obtained.

EXAMPLE 20

Analogously to Example 18, 143 mg (1.7 mmols) of 2-amino-1,3,4-triazole in 15 ml of 1 M HCl were diazotised with a solution of 127 mg (1.85 mmols) of sodium nitrite in 2 ml of water. As indicated in Example 18, urea and sodium hydroxide solution were added to the solution thus obtained and the resulting mixture was then combined with a solution of 1 g (0.154 mmol) of BPTI in 10 ml of 1 M sodium carbonate/potassium bicarbonate buffer of pH 9.5. After adding a small amount of phenol, the reaction solution was freed from salts by gel filtration through Sephadex ® G-10 and, after lyophilising, the eluate was chromatographed on Sephadex ® G-50, using 0.1 M acetic acid as the eluant, as already described in example 18. This gave 60 mg (6%) of substances of higher molecular weight and, from the main fraction, 810 mg (81%) of substance.

EXAMPLE 21

5.4 mg (64 μmols) of 5-aminotetrazole-(1,H) were diazotised in 1 ml of 1 M hydrochloric acid at +4° C. with 5 mg (70 μmols) of sodium nitrite. After reacting the excess nitrite with a small amount of amidosulphonic acid, the diazonium salt formed was stirred with 100 mg (15.4 μmols) of mononitro-BPTI (compare Example 13) in 10 ml of 1 M sodium carbonate solution at pH 10.0 for 15 minutes. Finally, a small amount of phenol was added. After the solution had been freed from salts by gel filtration through Sephadex ® G-10 using 0.1 M ammonium hydroxide solution as the eluant, the lyophilised eluate was chromatographed on Sephadex ® G-50. This gave 10 mg (10%) of substances of higher molecular weight and, from the main fraction, 68 mg (68%) of yellow substance.

EXAMPLE 22

27 mg (0.31 mmol) of 5-aminotetrazole-(1,H) were diazotised as indicated in Example 18. A small amount of amidosulphonic acid was added to the diazonium salt solution and the pH value was adjusted to 9.5 with concentrated sodium hydroxide solution. The solution thus obtained was combined, at +4° C., with a solution of 500 mg of dinitro-BPTI (see Example 14) in 15 ml of 1 M sodium carbonate buffer of pH 9.0. After stirring for 15 minutes at +4° C., the reaction solution was freed from salts by gel filtration through Sephadex ® G-10 (2.9 × 100 cm column), after previously adding a small amount of phenol to destroy the excess diazonium salt. The freeze-dried eluate was chromatographed on Sephadex ® G-50 using 0.1 M acetic acid as the eluant. This gave 25 mg (5%) of substances of higher molecular weight and, from the main fraction, 396 mg (79%) of substance.

EXAMPLE 23

Sodium nitrite solution was added to 500 mg of partially deamidised BPTI, obtained by leaving BPTI to stand for 20 days in 2 N hydrochloric acid (2 g/100 ml) at 20° C. and under nitrogen, in a solution containing acetic acid, as described in Example 3, and the mixture was reacted for 24 hours at +4° C. As indicated in Example 3, the reaction mixture was then concentrated to a volume of about 10 ml and freed from salts by filtration through Sephadex ® G-10 using 0.1 M aqueous ammonia as the eluant. The substance obtained by freeze-drying the fractions containing protein was chromatographed in 0.1 M acetic acid on Sephadex ® G-50 in order to separate off substances of higher molecular weight (about 36 mg = about 7%). 372 mg (74%) of substance were obtained when the main fraction was lyophilised.

What is claimed is:

1. A process for the preparation of a deamino kallikrein-trypsin inhibitor obtained from cattle organs which comprises reacting (a) a nitro derivative of BPTI or a deamido derivative of BPTI
   at a pH of from about 2 up to about 7 with a compound which supplies nitrous acid or nitrosyl ions at a temperature of from about −20° C. to about +30° C. and in the presence of an acid, or
   (b) reacting BPTI, a nitro derivative of BPTI or a deamido derivative of BPTI at a pH of from about 1 to about 12 with a diazonium compound at a temperature of from about −20° to about +30° C.

2. A process according to claim 1, wherein reaction (a) is carried out in the presence of a nucleophilic reagent.

3. A process according to claim 1, wherein reaction (b) is carried out under an inert gas or under vacuum.

4. A process according to claim 1, wherein the reaction (a) is carried out in an aqueous solution which contains an organic solvent.

5. A process according to claim 1, wherein compounds obtained from reaction (a) or (b) are treated to reduce any occurring nitro nitroso groups.

6. A process according to claim 1, wherein the reaction product is fractionated.

7. A process according to claim 1, wherein the compound supplying nitrous acid or nitrosyl ions is selected from the group consisting of salts of nitrous acid, nitrosylchloride, nitrosylsulphuric acid, and alkyl esters of nitrous acid.

8. A process according to claim 1, wherein the diazonium compound is a diazotised heterocyclic amine.

9. A pharmaceutical composition useful in the treatment of diseases caused by overproduction of proteases, comprising a therapeutically or prophylactically effective amount of the deamino kallikrein-trypsin inhibitor obtained from cattle organs having elastace inhibition activity, characterized by
   (a) 0 to 3 lysine residues and/or 3 to 6 arginine residues and/or 1 to 4 tyrosine residues; and
   (b) the 10- and/or 21-tyrosine residues being unsubstituted or substituted by at least one nitro, nitroso or amino in the ortho position relative to the phenolic hydroxy group, in combination with a pharmaceutically acceptable solid or liquid inert carrier or diluent therefor.

10. A composition according to claim 9, in the form of a sterile and isotonic aqueous solution.

11. A composition according to claim 9 containing from about 0.5 to about 95% by weight of the said deamino derivative.

12. A method of treating diseases caused by overproduction of proteases, which comprises administering to the host in need thereof a therapeutically or prophylactically effective amount of the deamino kallikrein-trypsin inhibitor obtained from cattle organs having elastace inhibition activity, characterized by
    (a) 0 to 3 lysine residues and/or 3 to 6 arginine residues and/or 1 to 4 tyrosine residues; and
    (b) the 10- and/or 21-tyrosine residues being unsubstituted or substituted by at least one nitro, nitroso or amino in the ortho position relative to the phenolic hydroxy group.

13. A method according to claim 12, in which the deamino derivative is administered in an amount of from about 0.1 to about 20 mg per kg body weight per day.

14. A method according to claim 12, in which the deamino compound is administered parenterally, topically or orally.

* * * * *

UNITED STATES PATENT AND TRADEMARK OFFICE
CERTIFICATE OF CORRECTION

PATENT NO. : 4,118,481

DATED : October 3, 1978

INVENTOR(S) : Eugen Schnabel, et al.

It is certified that error appears in the above-identified patent and that said Letters Patent are hereby corrected as shown below:

```
Title page Abstract "demaino" should be --deamino--.
Column 3, line 19, "Hornle" should be --Hörnle--
Column 3, line 25, "Hornle" should be --Hörnle--
Column 3, line 27, "Hornle" should be --Hörnle--.
Column 4, line 14, "HIggins" should be --Higgins--.
Column 4, line 65, "Athritis" 2nd occ. should be
   --Arthritis--.
Column 6, line 36, "Hornle" should be --Hörnle--.
Column 16, line 54, move "1.3" one column over and
   move "7.2" and 36.5 one column over.
Column 17, line 8, "Wister" should be --Wistar--
Column 18, line 17, "...reintryps in " should be
   --...reintrypsin--.
Column 28, line 3, insert --or-- after "nitro".
```

SEE ATTACHED PAGES OF COLUMNS 11, 12, 9 and 10 for changes in Tables 3, 4 and 5.

Signed and Sealed this

Thirteenth Day of March 1979

[SEAL]

Attest:

RUTH C. MASON
Attesting Officer

DONALD W. BANNER
Commissioner of Patents and Trademarks

Table 3

Percentage inhibition[1]) of 0.25 nkat of pancreas elastase (pig) by various deamino-BPTI derivatives using succinyl-L-alanyl-L-alanyl-L-alanine-p-nitroanilide as the substrate, determined by the method of J. Bieth et al. [Biochem.Med. 11, 350 (1974)] with a 15 minute pre-incubation (+) and without pre-incubation (-) of the enzyme and the inhibitor.

| Deamino-BPTI derivative prepared according to Example | | 50 µg | | 25 µg | | 12.5 µg | | 5 µg | | 2.5 µg | |
|---|---|---|---|---|---|---|---|---|---|---|---|
| | | + | - | + | - | + | - | + | - | + | - |
| 1 | Fraction A | 100 | 98 | 98 | 98 | 93 | 90 | 53 | 63 | 35 | 35 |
| | " B | | | | 100 | | 100 | | 76 | | 58 |
| | " C | | | | 100 | | 96 | | 73 | | 53 |
| | " D | | | | 100 | | 90 | | 60 | | 40 |
| | " E | | | | 100 | | 99 | | 69 | | 32 |
| | " F | | 87 | 86 | 64 | 87 | 40 | 74 | 28 | 44 | 10 | 21 |
| 2 | Fraction A | | | 100 | | 92 | | 70 | | 55 | | 31 |
| | " B | | | 99 | | 90 | | 75 | | 60 | | 30 |
| | " C | | | 100 | | 98 | | 90 | | 40 | | 34 |
| | " D | | | 100 | | 95 | | 85 | | 70 | | 52 |
| | " E | | | 100 | | 96 | | 90 | | 65 | | 30 |
| | " F | | | 100 | | 90 | | 78 | | 55 | | 38 |
| 3 | | 97 | 95 | 89 | 91 | 69 | 74 | 44 | 47 | 25 | 15 |
| 4 | | 97 | 99 | 90 | 92 | 76 | 73 | 50 | 48 | 33 | 38 |
| 5 | | 100 | 99 | 95 | 87 | 86 | 77 | 47 | 35 | 25 | 15 |
| 6 | | | 91 | | 85 | | 48 | | 21 | | 12 |
| 7 | | 97 | 97 | 82 | 90 | 75 | 77 | 44 | 35 | | |
| 10 | | 100 | 100 | 94 | 92 | 75 | 75 | 37 | 38 | 21 | 20 |
| 11 | | | 93 | | 85 | | 58 | | 17 | | 10 |
| 13 | | 100 | 100 | 96 | 92 | 91 | 72 | 48 | 37 | 29 | 13 |
| 14 | | 100 | 99 | 97 | 98 | 87 | 86 | 45 | 40 | 22 | 20 |
| 18 | | 84 | 97 | 77 | 70 | 55 | 51 | 42 | 26 | 26 | 19 |
| 21 | | 96 | 95 | 90 | 71 | 55 | 44 | 28 | 18 | 15 | 10 |
| 22 | | | 67 | | 45 | | 27 | | 12 | | - |

1) Calculated from: % inhibition = $\left(1 - \dfrac{\Delta \text{OD test}}{\Delta \text{OD enzyme control}}\right) \times 100$

Table 4

Percentage inhibition[1] of 0.25 nkat of pancreas elastase (pig) by several deamino-BPTI derivatives using soluble elastin as the substrate, by the method of S. Keller and I. Mandl [Biochem. Med. 5, 342 (1971)] with a 15 minute pre-incubation (+) or without pre-incubation (−) of the enzyme and the inhibitor.

| Deamino-BPTI derivative prepared according to Example | 50 µg | | 25 µg | | 12.5 µg | | 5 µg | | 2.5 µg | |
|---|---|---|---|---|---|---|---|---|---|---|
| | + | − | + | − | + | − | + | − | + | − |
| 3  | 97 | 94  | 94 | 88 | 92 | 84 | 59 | 45 | 38 | 20 |
| 4  | 95 | 98  | 94 | 92 | 86 | 82 | 52 | 55 | 46 | 39 |
| 5  |    | 97  |    | 94 |    | 92 |    | 51 |    | 23 |
| 6  |    | 98  |    | 92 |    | 82 |    | 38 |    | 15 |
| 7  | 97 | 98  | 96 | 97 | 89 | 90 | 65 | 50 | 41 | 28 |
| 10 |    | 97  |    | 91 |    | 82 |    | 33 |    | 18 |
| 11 |    | 98  |    | 96 |    | 88 |    | 43 |    | 20 |
| 13 | 97 | 97  | 92 | 93 | 89 | 85 | 59 | 64 | 36 | 31 |
| 14 | 96 | 100 | 88 | 98 | 73 | 84 | 36 | 43 | 18 | 23 |
| 17 | 87 | 81  | 81 | 79 | 75 | 70 | 64 | 53 | 28 | 25 |
| 21 | 96 | 86  | 90 | 84 | 65 | 83 | 54 | 59 | 31 | 25 |
| 22 |    | 68  |    | 39 |    | 20 |    | 15 |    | −  |

[1] Calculated from: % inhibition $= \left(1 - \dfrac{\Delta \text{OD test}}{\Delta \text{OD enzyme control}}\right) \times 100$

Table 5

Percentage inhibition[1]) of 0.25 nkat of granulocyte elastase (human) by various deamino-BPTI derivatives using succinyl-L-alanyl-L-alanyl-L-alanine-p-nitro-anilide as the substrate, determined by the method of J. Bieth et al. [Biochem. Med. 11, 350 (1974)] with a 15 minute pre-incubation (+) and without pre-incubation (−) of the enzyme and the inhibitor.

| Deamino-BPTI derivative prepared according to Example | | 50 µg + | 50 µg − | 25 µg + | 25 µg − | 12.5 µg + | 12.5 µg − | 5 µg + | 5 µg − |
|---|---|---|---|---|---|---|---|---|---|
| 1 | Fraction A | 88 | 73 | 55 | 60 | 38 | 44 | 17 | 18 |
| | " B | | 83 | | 49 | | 35 | | 20 |
| | " C | | 83 | | 53 | | 45 | | 10 |
| | " D | | 89 | | 62 | | 40 | | 21 |
| | " E | | 78 | | 48 | | 35 | | 9 |
| | " F | 55 | 60 | 39 | 42 | 28 | 29 | 6 | 7 |
| 2 | Fraction A | | 58 | | 38 | | 15 | | 8 |
| | " B | | 68 | | 43 | | 18 | | 4 |
| | " C | | 72 | | 55 | | 33 | | 11 |
| | " D | | 76 | | 55 | | 23 | | 6 |
| | " E | | 65 | | 45 | | 20 | | 8 |
| | " F | | 60 | | 47 | | 22 | | 5 |

| Deamino-BPTI derivative prepared according to Example | 50 µg + | 50 µg − | 25 µg + | 25 µg − | 12.5 µg + | 12.5 µg − | 5 µg + | 5 µg − |
|---|---|---|---|---|---|---|---|---|
| 3 | 68 | 71 | 43 | 50 | 23 | 26 | 15 | 10 |
| 4 | 72 | 74 | 43 | 43 | 27 | 33 | 18 | 14 |
| 5 | 72 | 75 | 46 | 45 | 26 | 26 | 13 | 11 |
| 6 | | 56 | | 31 | | 18 | | 8 |
| 10 | 69 | 66 | 48 | 45 | 27 | 32 | 14 | 14 |
| 13 | 83 | 78 | 55 | 53 | 35 | 22 | 20 | 10 |
| 14 | 81 | 74 | 55 | 44 | 34 | 31 | 19 | 15 |
| 18 | 63 | 61 | 45 | 43 | 28 | 29 | 17 | 16 |
| 21 | | 53 | | 29 | | 20 | | 9 |
| 22 | | 60 | | 46 | | 24 | | 9 |

1) Calculated from: % inhibition = $\left(1 - \dfrac{\Delta \text{OD test}}{\Delta \text{OD enzyme control}}\right) \times 100$